(12) United States Patent
Cheong et al.

(10) Patent No.: US 9,388,243 B2
(45) Date of Patent: *Jul. 12, 2016

(54) METHOD OF TARGET MEMBRANE PROTEIN DEPLETION

(71) Applicant: Samsung Electronics Co., Ltd., Suwon-si, Gyeonggi-do (KR)

(72) Inventors: Kwang Ho Cheong, Seoul (KR); Seung Hyun Lee, Suwon-si (KR); Mi Young Cho, Seoul (KR); Young Jun Koh, Yongin-si (KR); Lin Powei, Hwaseong-si (KR); Christina Yi, Seongnam-si (KR); Jae Woong Hwang, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/290,447

(22) Filed: May 29, 2014

(65) Prior Publication Data

US 2014/0356366 A1    Dec. 4, 2014

(30) Foreign Application Priority Data

May 29, 2013 (KR) ........................ 10-2013-0061282
May 27, 2014 (KR) ........................ 10-2014-0063899

(51) Int. Cl.
*C07K 16/28* (2006.01)
*C07K 16/32* (2006.01)

(52) U.S. Cl.
CPC ............. *C07K 16/2863* (2013.01); *C07K 16/32* (2013.01); *C07K 2317/24* (2013.01); *C07K 2317/31* (2013.01); *C07K 2317/34* (2013.01); *C07K 2317/52* (2013.01); *C07K 2317/53* (2013.01); *C07K 2317/622* (2013.01); *C07K 2317/73* (2013.01); *C07K 2317/76* (2013.01); *C07K 2317/77* (2013.01); *C07K 2317/92* (2013.01)

(58) Field of Classification Search
CPC ............... C07K 16/2863; C07K 16/32; C07K 2317/24; C07K 2317/31; C07K 2317/34; C07K 2317/52; C07K 2317/53; C07K 2317/622; C07K 2317/73; C07K 2317/76; C07K 2317/77; C07K 2317/92
See application file for complete search history.

(56) References Cited

U.S. PATENT DOCUMENTS

| 7,514,545 | B2 | 4/2009 | Fandl et al. | |
|---|---|---|---|---|
| 2002/0086356 | A1 | 7/2002 | Tuschl et al. | |
| 2004/0241158 | A1* | 12/2004 | McBride et al. | ........... 424/130.1 |
| 2009/0035849 | A1 | 2/2009 | Rice et al. | |
| 2010/0254988 | A1 | 10/2010 | Bossenmaier et al. | |
| 2010/0256339 | A1 | 10/2010 | Bossenmaier et al. | |
| 2011/0262436 | A1* | 10/2011 | Bender et al. | .............. 424/133.1 |
| 2013/0089557 | A1 | 4/2013 | Cheong et al. | |

FOREIGN PATENT DOCUMENTS

| EP | 2764024 A1 | 8/2014 |
|---|---|---|
| KR | 2013-0037189 A | 4/2013 |
| WO | WO 2009/149185 A2 | 12/2009 |
| WO | WO 2012/106587 A1 | 8/2012 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Choi HJ, et al., Mol. Cancer Ther., 12(12):2748-2759, Dec. 2013. Available online at—doi: 10.1158/1535-7163.MCT-13/0628.*
Spiess C, et al., Nature Biotechnology, 31:753-758, 2013. Available online at—doi:10.1038/nbt.2621.*
Thakur et al., "Cancer therapy with bispecific antibodies: Clinical experience", *Current Opinion in Molecular Therapeutics*, 12(3), 340-349 (2010).
European Search Report for Application No. 14170524.4 dated Oct. 8, 2014.

* cited by examiner

*Primary Examiner* — Robert Landsman
(74) *Attorney, Agent, or Firm* — Leydig, Voit & Mayer, Ltd.

(57) ABSTRACT

A method of target membrane protein depletion comprising treating a cell with a dual binding molecule comprising a first binding domain which binds to a driver membrane protein and a second binding domain which binds to a target membrane protein, wherein the cell comprises a cell membrane, and the driver membrane protein and target membrane protein are associated with the cell membrane where the target membrane protein positions, and are internalized into a cell and degraded when the first binding domain of the dual binding molecule binds the driver membrane protein; as well as related methods and compositions.

12 Claims, 13 Drawing Sheets
(5 of 13 Drawing Sheet(s) Filed in Color)

SEQUENCE LISTING

```
<160> NUMBER OF SEQ ID NOS: 138

<210> SEQ ID NO 1
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2
```

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
<220> FEATURE:
<221> NAME/KEY: MOD_RES
<222> LOCATION: (1)..(1)
<223> OTHER INFORMATION: Xaa is Pro or Ser or absent
<220> FEATURE:
<221> NAME/KEY: MOD_RES
<222> LOCATION: (2)..(2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MOD_RES
<222> LOCATION: (3)..(3)
<223> OTHER INFORMATION: Xaa is Asn or Lys
<220> FEATURE:
<221> NAME/KEY: MOD_RES
<222> LOCATION: (4)..(4)
<223> OTHER INFORMATION: Xaa is Ala or Val
<220> FEATURE:
<221> NAME/KEY: MOD_RES
<222> LOCATION: (7)..(7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: MOD_RES
<222> LOCATION: (5)..(5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MOD_RES
<222> LOCATION: (4)..(4)
<223> OTHER INFORMATION: Xaa is His, Arg, Gln or Lys
<220> FEATURE:
<221> NAME/KEY: MOD_RES
<222> LOCATION: (9)..(9)
<223> OTHER INFORMATION: Xaa is Ser or Trp
<220> FEATURE:
<221> NAME/KEY: MOD_RES
<222> LOCATION: (12)..(12)
<223> OTHER INFORMATION: Xaa is His or Gln
<220> FEATURE:
<221> NAME/KEY: MOD_RES
<222> LOCATION: (13)..(13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MOD_RES
<222> LOCATION: (2)..(2)
<223> OTHER INFORMATION: Xaa is Ala or Gly
<220> FEATURE:
<221> NAME/KEY: MOD_RES
<222> LOCATION: (4)..(4)
<223> OTHER INFORMATION: Xaa is Thr or Lys
<220> FEATURE:
<221> NAME/KEY: MOD_RES
<222> LOCATION: (7)..(7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MOD_RES
<222> LOCATION: (1)..(1)
<223> OTHER INFORMATION: Xaa is Gly, Ala or Gln
<220> FEATURE:
<221> NAME/KEY: MOD_RES
<222> LOCATION: (6)..(6)
<223> OTHER INFORMATION: Xaa is Arg, His, Ser, Ala, Gly or Lys
<220> FEATURE:
<221> NAME/KEY: MOD_RES
<222> LOCATION: (8)..(8)
<223> OTHER INFORMATION: Xaa is Leu, Tyr, Phe or Met

```
<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)
```

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti
      c-Met humanized antibody (huAbF46-H4))

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
            85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
            85                  90                  95

Ser Tyr Ser His Pro Phe Ser Phe Gly Gln Gly Thr Lys Val Glu Ile
            100                 105                 110

Lys Arg

<210> SEQ ID NO 21

```
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)
```

```
<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
```

```
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15
Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1               5                   10                  15
Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1               5
```

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38

```
gaattcgccg ccaccatgga atggagctgg gttttctcg taacactttt aaatggtatc    60
cagtgtgagg tgaagctggt ggagtctgga ggaggcttgg tacagcctgg gggttctctg   120
agactctcct gtgcaacttc tgggttcacc ttcactgatt actacatgag ctgggtccgc   180
cagcctccag gaaaggcact tgagtggttg ggttttatta gaaacaaagc taatggttac   240
acaacagagt acagtgcatc tgtgaagggt cggttcacca tctccagaga taattcccaa   300
agcatcctct atcttcaaat ggacaccctg agagctgagg acagtgccac ttattactgt   360
gcaagagata ctggtttgc ttactggggc aagggactc tggtcactgt ctctgcagct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttcccccc aaaacccaag gacaccctca tgatctcccg gaccctgag   840
```

```
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416

<210> SEQ ID NO 39
<211> LENGTH: 759
<212> TYPE: DNA
<213> ORGANISM: Artificial Sequence
<220> FEATURE:
<223> OTHER INFORMATION: Synthetic (nucleotide sequence of light chain
      of chAbF46)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga gaaggtcact atgagctgca gtccagtca gagtctttta    180 gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
```
gagcaggaca gcaaggacag cacctacagc ctcagcagca ccctgacgct gagcaaagca    660
gactacgaga acacaaagt ctacgcctgc gaagtcaccc atcagggcct gagctcgccc    720
gtcacaaaga gcttcaacag gggagagtgt tgactcgag                           759

<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

```
Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
            210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light)

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
            210                 215                 220

<210> SEQ ID NO 45
```

```
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
```

|  | 100 |  |  |  | 105 |  |  |  | 110 |  |  |
|---|---|---|---|---|---|---|---|---|---|---|---|
| Lys | Arg | Thr | Val | Ala | Ala | Pro | Ser | Val | Phe | Ile | Phe | Pro | Pro | Ser | Asp |

Lys Arg Thr Val Ala Ala Pro Ser Val Phe Ile Phe Pro Pro Ser Asp
                115                          120                          125

Glu Gln Leu Lys Ser Gly Thr Ala Ser Val Val Cys Leu Leu Asn Asn
    130                          135                          140

Phe Tyr Pro Arg Glu Ala Lys Val Gln Trp Lys Val Asp Asn Ala Leu
145                         150                          155                          160

Gln Ser Gly Asn Ser Gln Glu Ser Val Thr Glu Gln Asp Ser Lys Asp
                165                        170                          175

Ser Thr Tyr Ser Leu Ser Ser Thr Leu Thr Leu Ser Lys Ala Asp Tyr
            180                        185                          190

Glu Lys His Lys Val Tyr Ala Cys Glu Val Thr His Gln Gly Leu Ser
        195                        200                          205

Ser Pro Val Thr Lys Ser Phe Asn Arg Gly Glu
    210                          215

<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47

```
gaggtgcagc tggtggagtc tggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180
gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt tgcttactg ggtcaagga accctggtca ccgtctcctc ggctagcacc      360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660
gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc ccatcgaga aaaccatctc caaagccaaa      1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctccctgt ctccgggtaa atgactcgag                                     1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48

| | | | | | |
|---|---|---|---|---|---|
| gaggtgcagc | tggtggagtc | tgggggaggc | ttggtccagc | ctggagggtc | cctgagactc | 60 |
| tcctgtgcag | cctctggatt | caccttcact | gactactaca | tgagctgggt | ccgccaggct | 120 |
| ccagggaagg | ggctggagtg | gttgggcttt | attagaaaca | aagctaacgg | ttacaccaca | 180 |
| gaatacagtg | cgtctgtgaa | aggcagattc | accatctcaa | gagataattc | aaagaactca | 240 |
| ctgtatctgc | aaatgaacag | cctgcgtgct | gaggacacgg | ccgtgtatta | ctgtgctaga | 300 |
| gataactggt | ttgcttactg | gggtcaagga | accctggtca | ccgtctcctc | ggctagcacc | 360 |
| aagggcccat | cggtcttccc | cctggcaccc | tcctccaaga | gcacctctgg | ggcacagcg | 420 |
| gccctgggct | gcctggtcaa | ggactacttc | cccgaaccgg | tgacggtgtc | gtggaactca | 480 |
| ggcgccctga | ccagcggcgt | gcacaccttc | ccggctgtcc | tacagtcctc | aggactctac | 540 |
| tccctcagca | gcgtggtgac | cgtgccctcc | agcagcttgg | gcacccagac | ctacatctgc | 600 |
| aacgtgaatc | acaagcccag | caacaccaag | gtggacaaga | aagttgagcc | caaatcttgt | 660 |
| gacaaaactc | acacatgccc | accgtgccca | gcacctgaac | tcctggggg | accgtcagtc | 720 |
| ttcctcttcc | ccccaaaacc | caaggacacc | ctcatgatct | cccggacccc | tgaggtcaca | 780 |
| tgcgtggtgg | tggacgtgag | ccacgaagac | cctgaggtca | agttcaactg | gtacgtggac | 840 |
| ggcgtggagg | tgcataatgc | caagacaaag | ccgcgggagg | agcagtacaa | cagcacgtac | 900 |
| cgtgtggtca | gcgtcctcac | cgtcctgcac | caggactggc | tgaatggcaa | ggagtacaag | 960 |
| tgcaaggtct | ccaacaaagc | cctcccagcc | cccatcgaga | aaaccatctc | caaagccaaa | 1020 |
| gggcagcccc | gagaaccaca | ggtgtacacc | ctgcccccat | cccgggagga | gatgaccaag | 1080 |
| aaccaggtca | gcctgacctg | cctggtcaaa | ggcttctatc | ccagcgacat | cgccgtggag | 1140 |
| tgggagagca | atgggcagcc | ggagaacaac | tacaagacca | cgcctcccgt | gctggactcc | 1200 |
| gacggctcct | tcttcctcta | cagcaagctc | accgtggaca | agagcaggtg | gcagcagggg | 1260 |
| aacgtcttct | catgctccgt | gatgcatgag | gctctgcaca | accactacac | gcagaagagc | 1320 |
| ctctccctgt | ctccgggtaa | atgactcgag | | | | 1350 |

<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49

| | | | | | |
|---|---|---|---|---|---|
| gaggttcagc | tggtggagtc | tggcggtggc | ctggtgcagc | caggggggctc | actccgtttg | 60 |
| tcctgtgcag | cttctggctt | caccttcact | gattactaca | tgagctgggt | gcgtcaggcc | 120 |
| ccgggtaagg | gcctggaatg | gttgggtttt | attagaaaca | aagctaatgg | ttacacaaca | 180 |
| gagtacagtg | catctgtgaa | gggtcgtttc | actataagca | gagataattc | caaaaacaca | 240 |
| ctgtacctgc | agatgaacag | cctgcgtgct | gaggacactg | ccgtctatta | ttgtgctaga | 300 |
| gataactggt | ttgcttactg | gggccaaggg | actctggtca | ccgtctcctc | ggctagcacc | 360 |
| aagggcccat | cggtcttccc | cctggcaccc | tcctccaaga | gcacctctgg | ggcacagcg | 420 |

```
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc cccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atgactcgag                                      1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50

```
gacatcgtga tgacccagtc tccagactcc ctggctgtgt ctctgggcga gagggccacc    60
atcaactgca agtccagcca gagtctttta gctagcggca accaaaataa ctacttagct    120
tggcaccagc agaaaccagg acagcctcct aagatgctca ttatttgggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                             669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51

```
gatattgtga tgacccagac tccactctcc ctgcccgtca cccctggaga gccggcctcc    60
```

| | |
|---|---|
| atctcctgca agtccagtca gagtcttta gctagtggca accaaaataa ctacttggcc | 120 |
| tggcacctgc agaagccagg gcagtctcca cagatgctga tcatttgggc atccactagg | 180 |
| gtatctggag tcccagacag gttcagtggc agtgggtcag gcactgattt cacactgaaa | 240 |
| atcagcaggg tggaggctga ggatgttgga gtttattact gccagcagtc ctacagcgct | 300 |
| ccgctcacgt tcggacaggg taccaagctg gagctcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 52
<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52

| | |
|---|---|
| gacatcgtga tgacccagtc tccagactcc ctggctgtgt ctctgggcga gagggccacc | 60 |
| atcaactgca gtccagcca gagtcttta gctagcggca accaaaataa ctacttagct | 120 |
| tggtaccagc agaaaccagg acagcctcct aagctgctca ttatttgggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

| | |
|---|---|
| gatatccaga tgacccagtc cccgagctcc ctgtccgcct ctgtgggcga tagggtcacc | 60 |
| atcacctgca gtccagtca gagtcttta gctagtggca accaaaataa ctacttggcc | 120 |
| tggcaccaac agaaaccagg aaaagctccg aaaatgctga ttatttgggc atccactagg | 180 |
| gtatctggag tccttctcg cttctctgga tccgggtctg gacggatttt cactctgacc | 240 |
| atcagcagtc tgcagccgga agacttcgca acttattact gtcagcagtc ctacagcgct | 300 |
| ccgctcacgt tcggacaggg taccaaggtg gagatcaaac gtacggtggc tgcaccatct | 360 |
| gtcttcatct tcccgccatc tgatgagcag ttgaaatctg gaactgcctc tgttgtgtgc | 420 |

```
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc       600 gaagtcaccc atcagggcct gagctcgccc gtcacaaaga gcttcaacag gggagagtgt      660
tgactcgag                                                              669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

```
Gly Leu Gly Gly Leu Gly Gly Gly Ser Gly Gly Gly Gly Ser Gly
 1               5                  10                  15

Gly Ser Ser Gly Val Gly Ser
            20
```

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of
      huAbF46 antibody)

<400> SEQUENCE: 55

```
gctagcgttt tagcagaagt tcaattggtt gaatctggtg gtggtttggt tcaaccaggt       60
ggttctttga dattgtcttg tgctgcttct ggttttactt tcaccgatta ttacatgtcc      120
tgggttagac aagctccagg taaaggtttg aatggttgg gtttcattag aaacaaggct       180
aacggttaca ctaccgaata ttctgcttct gttaagggta gattcaccat ttctagagac      240
aactctaaga cacccttgta cttgcaaatg aactccttga gagctgaaga tactgctgtt      300
tattactgcg ctagagataa ttggtttgct tattggggtc aaggtacttt tggttactgtt     360 tcttctggcc tcgggggcct cggaggagga ggtagtggcg gaggaggctc cggtggatcc      420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact ggcttggca tcaacaaaaa ccaggtaaag ctccaaagat gttgattatt      600
tgggcttcta ccagagtttc tggtgttcca tctagatttt ctggttctgg ttccggtact     660 gatttttactt tgaccatttc atccttgcaa ccagaagatt tcgctactta ctactgtcaa    720
caatcttact ctgctccatt gacttttggt caaggtacaa aggtcgaaat caagagagaa    780
ttcggtaagc ctatccctaa ccctctcctc ggtctcgatt ctacgggtgg tgtggatct      840 ggtggtggtg gttctggtgg tggtggttct caggaactga caactatatg cgagcaaatc   900
ccctcaccaa ctttagaatc gacgccgtac tctttgtcaa cgactactat tttggccaac     960
gggaaggcaa tgcaaggagt ttttgaatat acaaatcag taacgtttgt cagtaattgc     1020
ggttctcacc cctcaacaac tagcaaaggc agccccataa acacacagta tgttttttga    1080
gtttaaac                                                             1088
```

<210> SEQ ID NO 56
<211> LENGTH: 5597

```
<212> TYPE: DNA
<213> ORGANISM: Artificial Sequence
<220> FEATURE:
<223> OTHER INFORMATION: Synthetic (expression vector including
      polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agcctatttt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata ttttctgtta ttgctagcgt tttagcagaa gttcaattgg     600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactccct tgagagctgaa gatactgctg tttattactg cgctagagat aattggtttg     900
cttattgggg tcaaggtact ttggttactg tttcttctgg cctcgggggc ctcggaggag     960
```

-continued

```
gaggtagtgg cggaggaggc tccggtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
aaccaggtaa agctccaaag atgttgatta tttgggcttc taccagagtt tctggtgttc    1200
catctagatt ttctggttct ggttccggta ctgattttac tttgaccatt tcatccttgc    1260
aaccagaaga tttcgctact tactactgtc aacaatctta ctctgctcca ttgacttttg    1320
gtcaaggtac aaaggtcgaa atcaagagag aattcggtaa gcctatccct aaccctctcc    1380
tcggtctcga ttctacgggt ggtggtggat ctggtggtgg tggttctggt ggtggtggtt    1440
ctcaggaact gacaactata tgcgagcaaa tcccctcacc aactttagaa tcgacgccgt    1500
actctttgtc aacgactact attttggcca acgggaaggc aatgcaagga gttttttgaat   1560 attacaaatc agtaacgttt gtcagtaatt gcggttctca cccctcaaca actagcaaag    1620
gcagccccat aaacacacag tatgtttttt gagtttaaac ccgctgatct gataacaaca    1680
gtgtagatgt aacaaaatcg actttgttcc cactgtactt ttagctcgta caaaatacaa    1740
tatacttttc atttctccgt aaacaacatg ttttcccatg taatatcctt ttctattttt    1800
cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcattttga    2040 cgaaatttgc tattttgtta gagtctttta caccatttgt ctccacacct ccgcttacat    2100
caacaccaat aacgccattt aatctaagcg catcaccaac attttctggc gtcagtccac    2160
cagctaacat aaaatgtaag ctctcggggc tctcttgcct tccaacccag tcagaaatcg    2220
agttccaatc caaaagttca cctgtcccac ctgcttctga atcaaacaag gaataaacg     2280 aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa acatcctcc ttaggttgat    2460 tacgaaacac gccaaccaag tatttcggag tgcctgaact attttttatat gcttttacaa   2520 gacttgaaat tttccttgca ataaccgggt caattgttct ctttctattg ggcacacata    2580
taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctccttt cttttttcga ccgaatttct tgaagacgaa agggcctcgt     2820
gatacgccta ttttatagg ttaatgtcat gataataatg gtttcttagg acggatcgct     2880
tgcctgtaac ttacacgcgc ctcgtatctt ttaatgatgg aataatttgg gaatttactc    2940
tgtgtttatt tatttttatg ttttgtattt ggatttttaga aagtaaataa agaaggtaga   3000
agagttacgg aatgaagaaa aaaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaggt agtatttgtt     3240 ggcgatcccc ctagagtctt ttacatcttc ggaaaacaaa aactattttt tctttaattt    3300
```

```
cttttttttac tttctatttt taatttatat atttatatta aaaaatttaa attataatta   3360
tttttatagc acgtgatgaa aaggacccag gtggcactttt tcggggaaat gtgcgcggaa   3420
cccctatttg tttattttc taaatacatt caaatatgta tccgctcatg agacaataac    3480
cctgataaat gcttcaataa tattgaaaaa ggaagagtat gagtattcaa catttccgtg   3540
tcgcccttat tccctttttt gcggcatttt gccttcctgt ttttgctcac ccagaaacgc   3600
tggtgaaagt aaaagatgct gaagatcagt tgggtgcacg agtgggttac atcgaactgg   3660
atctcaacag cggtaagatc cttgagagtt ttcgccccga agaacgtttt ccaatgatga   3720
gcacttttaa agttctgcta tgtggcgcgg tattatcccg tgttgacgcc gggcaagagc   3780
aactcggtcg ccgcatacac tattctcaga atgacttggt tgagtactca ccagtcacag   3840
aaaagcatct tacgatggc atgacagtaa gagaattatg cagtgctgcc ataaccatga    3900
gtgataacac tgcggccaac ttacttctga caacgatcgg aggaccgaag gagctaaccg   3960
cttttttgca acatggggg gatcatgtaa ctcgccttga tcgttgggaa ccggagctga    4020
atgaagccat accaaacgac gagcgtgaca ccacgatgcc tgtagcaatg gcaacaacgt   4080
tgcgcaaact attaactggc gaactactta ctctagcttc ccggcaacaa ttaatagact   4140
ggatggaggc ggataaagtt gcaggaccac ttctgcgctc ggcccttccg gctggctggt   4200
ttattgctga taaatctgga gccggtgagc gtgggtctcg cggtatcatt gcagcactgg   4260
ggccagatgg taagccctcc cgtatcgtag ttatctacac gacgggcagt caggcaacta   4320
tggatgaacg aaatagacag atcgctgaga taggtgcctc actgattaag cattggtaac   4380
tgtcagacca agtttactca tatatacttt agattgattt aaaacttcat ttttaattta   4440
aaaggatcta ggtgaagatc ctttttgata atctcatgac caaaatccct taacgtgagt   4500
tttcgttcca ctgagcgtca gaccccgtag aaaagatcaa aggatcttct tgagatcctt   4560 ttttttctgcg cgtaatctgc tgcttgcaaa caaaaaaacc accgctacca gcggtggttt   4620
gtttgccgga tcaagagcta ccaactcttt ttccgaaggt aactggcttc agcagagcgc   4680
agataccaaa tactgtcctt ctagtgtagc cgtagttagg ccaccacttc aagaactctg   4740
tagcaccgcc tacatacctc gctctgctaa tcctgttacc agtggctgct gccagtggcg   4800
ataagtcgtg tcttaccggg ttggactcaa gacgatagtt accggataag gcgcagcggt   4860
cgggctgaac ggggggttcg tgcacacagc ccagcttgga gcgaacgacc tacaccgaac   4920
tgagatacct acagcgtgag cattgagaaa gcgccacgct tcccgaaggg agaaaggcgg   4980
acaggtatcc ggtaagcggc agggtcggaa caggagagcg cacgagggag cttccagggg   5040
ggaacgcctg gtatctttat agtcctgtcg ggtttcgcca cctctgactt gagcgtcgat   5100
ttttgtgatg ctcgtcaggg gggcggagcc tatggaaaaa cgccagcaac gcggcctttt   5160
tacggttcct ggccttttgc tggccttttg ctcacatgtt ctttcctgcg ttatcccctg   5220
attctgtgga taaccgtatt accgcctttg agtgagctga taccgctcgc cgcagccgaa   5280
cgaccgagcg cagcgagtca gtgagcgagg aagcggaaga gcgcccaata cgcaaaccgc   5340
ctctccccgc gcgttggccg attcattaat gcagctggca cgacaggttt cccgactgga   5400
aagcgggcag tgagcgcaac gcaattaatg tgagttacct cactcattag gcaccccagg   5460
ctttacactt tatgcttccg gctcctatgt tgtgtggaat tgtgagcgga taacaatttc   5520
acacaggaaa cagctatgac catgattacg ccaagctcgg aattaaccct cactaaaggg   5580
aacaaaagct ggctagt                                                  5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-1 clone)

<400> SEQUENCE: 58
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca gtccagtca gagtcttta      180 gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtcagcagtc ctacagccgc ccgtacacgt tcggacaggg taccaaggtg     420
gagatcaaac gtacg                                                      435

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-2 clone)

<400> SEQUENCE: 59
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca gtccagtca gagtcttta      180 gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtgggcagtc ctacagccgt ccgctcacgt tcggacaggg taccaaggtg     420
gagatcaaac gtacg                                                      435

<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-3 clone)

<400> SEQUENCE: 60
gaattcacta gtgattaatt cgccgccacc atggattcac aggcccaggt cctcatgttg      60

-continued

```
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-5 clone)

<400> SEQUENCE: 61

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc cgtttacgt tcggacaggg taccaaggtg    420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy chain of huAbF46-H4-A1, U6-HC7 hinge and constant region of human IgG1)

<400> SEQUENCE: 62

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140
```

Leu Ala Pro Ser Ser Lys Ser Thr Gly Gly Thr Ala Ala Leu Gly
145                 150                 155                 160

Cys Leu Val Lys Asp Tyr Phe Pro Glu Pro Val Thr Val Ser Trp Asn
            165                 170                 175

Ser Gly Ala Leu Thr Ser Gly Val His Thr Phe Pro Ala Val Leu Gln
        180                 185                 190

Ser Ser Gly Leu Tyr Ser Leu Ser Ser Val Val Thr Val Pro Ser Ser
    195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide
      consisting of heavy chain of bF46-H4-A1, U6-HC7
      hinge and constant region of human IgG1)

<400> SEQUENCE: 63
gaattcgccg ccaccatgga atggagctgg gttttcctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180

```
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcacctcct ccaagagcac ctctgggggc     480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga tgaccaag     1140 aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg    1320 aacgtcttct catgctccgt gatgcatgag gctctgcaca accactacac gcagaagagc   1380 ctctcccctgt ctccgggtaa atgactcgag                                   1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region of
      human IgG)

<400> SEQUENCE: 64

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro

```
                130             135             140
Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
        290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
                340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
      consisting of heavy chain of huabF46-H4-A1, human IgG2
      hinge and constant region of human IgG1)

<400> SEQUENCE: 65
gaattcgccg ccaccatgga atggagctgg gttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
```

-continued

```
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgccccc ctgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg actcgag                                        1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region
      of human IgG2)

<400> SEQUENCE: 66

```
Met Glu Trp Ser Trp Val Phe Leu Val Thr Leu Leu Asn Gly Ile Gln
1               5                   10                  15

Cys Glu Val Gln Leu Val Glu Ser Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125
```

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
                195                 200                 205

Asn Phe Gly Thr Gln Thr Tyr Thr Cys Asn Val Asp His Lys Pro Ser
210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Gln Phe
                275                 280                 285

Asn Trp Tyr Val Asp Gly Val Glu Val His Asn Ala Lys Thr Lys Pro
290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
                340                 345                 350

Lys Gly Gln Pro Arg Glu Pro Gln Val Tyr Thr Leu Pro Pro Ser Arg
                355                 360                 365

Glu Glu Met Thr Lys Asn Gln Val Ser Leu Thr Cys Leu Val Lys Gly
                370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide
      consisting of heavy chain of uAbF46-H4-A1, human IgG2
      hinge and constant region of human IgG2)

<400> SEQUENCE: 67
gaattcgccg ccaccatgga atggagctgg gttttctcg taacactttt aaatggtatc        60
cagtgtgagg ttcagctggt ggagtctggc ggtggcctgg tgcagccagg gggctcactc      120

```
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc aagggactc tggtcaccgt ctcctcggct    420
agcaccaagg gcccatcggt cttccccctg gcgccctgct ccaggagcac ctccgagagc    480
acagcggccc tgggctgcct ggtcaaggac tacttccccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca cttcggcac ccagacctac    660 acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa acccaaggga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac acaggtgta cccctgccc catcccggg aggagatgac caagaaccag    1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                           1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1(H36Y) and human kappa constant region)

<400> SEQUENCE: 68

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125
```

```
Lys Val Glu Ile Lys Arg Thr Val Ala Ala Pro Ser Val Phe Ile Phe
            130                 135                 140
Pro Pro Ser Asp Glu Gln Leu Lys Ser Gly Thr Ala Ser Val Val Cys
145                 150                 155                 160
Leu Leu Asn Asn Phe Tyr Pro Arg Glu Ala Lys Val Gln Trp Lys Val
                165                 170                 175
Asp Asn Ala Leu Gln Ser Gly Asn Ser Gln Glu Ser Val Thr Glu Gln
            180                 185                 190
Asp Ser Lys Asp Ser Thr Tyr Ser Leu Ser Ser Thr Leu Thr Leu Ser
        195                 200                 205
Lys Ala Asp Tyr Glu Lys His Lys Val Tyr Ala Cys Glu Val Thr His
    210                 215                 220
Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic (polynucleotide encoding polypeptide
      consisting of light chain of huAbF46-H4-A1(H36Y) and human kappa
      constant region)

<400> SEQUENCE: 69

```
aattcactag tgattaattc gccgccacca tggattcaca ggcccaggtc ctcatgttgc    60
tgctgctatc ggtatctggt acctgtggag atatccagat gacccagtcc ccgagctccc   120
tgtccgcctc tgtgggcgat agggtcacca tcacctgcaa gtccagtcag agtcttttag   180
ctagtggcaa ccaaaataac tacttggcct ggtaccaaca gaaaccagga aaagctccga   240
aaatgctgat tatttgggca tccactaggg tatctggagt cccttctcgc ttctctggat   300
ccgggtctgg gacggatttc actctgacca tcagcagtct gcagccggaa gacttcgcaa   360
cttattactg tcagcagtcc tacagccgcc gtacacgttc ggacagggt accaaggtgg   420
agatcaaacg tacggtggct gcaccatctg tcttcatctt cccgccatct gatgagcagt   480
tgaaatctgg aactgcctct gttgtgtgcc tgctgaataa cttctatccc agagaggcca   540
aagtacagtg gaaggtggat aacgccctcc aatcgggtaa ctcccaggag agtgtcacag   600
agcaggacag caaggacagc acctacagcc tcagcagcac cctgacgctg agcaaagcag   660
actacgagaa acacaaagtc tacgcctgcg aagtcaccca tcagggcctg agctcgcccg   720
tcacaaagag cttcaacagg ggagagtgtt gactcgag                          758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1and human kappa constant region)

<400> SEQUENCE: 70

```
Met Asp Ser Gln Ala Gln Val Leu Met Leu Leu Leu Leu Ser Val Ser
1               5                   10                  15
Gly Thr Cys Gly Asp Ile Gln Met Thr Gln Ser Pro Ser Ser Leu Ser
            20                  25                  30
Ala Ser Val Gly Asp Arg Val Thr Ile Thr Cys Lys Ser Ser Gln Ser
        35                  40                  45
```

-continued

```
Leu Leu Ala Ser Gly Asn Gln Asn Asn Tyr Leu Ala Trp His Gln Gln
 50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
 1               5                  10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72

Pro Gln Ile Glu Glu Pro Ser Gln Cys Pro
 1               5                  10

<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
 1               5

<210> SEQ ID NO 74
```

```
<211> LENGTH: 117
<212> TYPE: PRT
<213> ORGANISM: Artificial Sequence
<220> FEATURE:
<223> OTHER INFORMATION: Synthetic (heavy chain variable region of
      anti-c-Met antibody (AbF46 or huAbF46-H1))

<400> SEQUENCE: 74
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

```
<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody (AbF46 or huAbF46-H1))

<400> SEQUENCE: 75
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

```
<210> SEQ ID NO 76
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
```

<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76

| | | | | | |
|---|---|---|---|---|---|
| gaattcgccg | ccaccatgga | atggagctgg | gttttctctg | taacactttt | aaatggtatc | 60 |
| cagtgtgagg | tgaagctggt | ggagtctgga | ggaggcttgg | tacagcctgg | gggttctctg | 120 |
| agactctcct | gtgcaacttc | tgggttcacc | ttcactgatt | actacatgag | ctgggtccgc | 180 |
| cagcctccag | aaaggcact | tgagtggttg | ggttttatta | gaaacaaagc | taatggttac | 240 |
| acaacagagt | acagtgcatc | tgtgaagggt | cggttcacca | tctccagaga | taattcccaa | 300 |
| agcatcctct | atcttcaaat | ggacaccctg | agagctgagg | acagtgccac | ttattactgt | 360 |
| gcaagagata | ctggtttgc | ttactggggc | caagggactc | tggtcactgt | ctctgcagct | 420 |
| agcaccaagg | gcccatcggt | cttccccctg | gcaccctcct | ccaagagcac | ctctgggggc | 480 |
| acagcggccc | tgggctgcct | ggtcaaggac | tacttcccg | aaccggtgac | ggtgtcgtgg | 540 |
| aactcaggcg | ccctgaccag | cggcgtgcac | accttcccgg | ctgtcctaca | gtcctcagga | 600 |
| ctctactccc | tcagcagcgt | ggtgaccgtg | ccctccagca | gcttgggcac | ccagacctac | 660 |
| atctgcaacg | tgaatcacaa | gcccagcaac | accaaggtgg | acaagaaagt | tgagcccaaa | 720 |
| tcttgtgaca | aaactcacac | atgcccaccg | tgcccagcac | ctgaactcct | ggggggaccg | 780 |
| tcagtcttcc | tcttcccccc | aaaacccaag | gacaccctca | tgatctcccg | gacccctgag | 840 |
| gtcacatgcg | tggtggtgga | cgtgagccac | gaagaccctg | aggtcaagtt | caactggtac | 900 |
| gtggacggcg | tggaggtgca | taatgccaag | acaaagccgc | gggaggagca | gtacaacagc | 960 |
| acgtaccgtg | tggtcagcgt | cctcaccgtc | ctgcaccagg | actggctgaa | tggcaaggag | 1020 |
| tacaagtgca | aggtctccaa | caaagccctc | ccagccccca | tcgagaaaac | catctccaaa | 1080 |
| gccaaagggc | agccccgaga | accacaggtg | tacaccctgc | ccccatcccg | ggaggagatg | 1140 |
| accaagaacc | aggtcagcct | gacctgcctg | gtcaaaggct | tctatcccag | cgacatcgcc | 1200 |
| gtggagtggg | agagcaatgg | gcagccggag | aacaactaca | agaccacgcc | tcccgtgctg | 1260 |
| gactccgacg | gctccttctt | cctctacagc | aagctcaccg | tggacaagag | caggtggcag | 1320 |
| caggggaacg | tcttctcatg | ctccgtgatg | catgaggctc | tgcacaacca | ctacacgcag | 1380 |
| aagagcctct | ccctgtctcc | gggtaaatga | ctcgag | | | 1416 |

<210> SEQ ID NO 77
<211> LENGTH: 759
<212> TYPE: DNA

```
<213> ORGANISM: Artificial Sequence
<220> FEATURE:
<223> OTHER INFORMATION: Synthetic (nucleotide sequence of light chain
      of anti-c-Met antibody (AbF46 or huAbF46-H1))
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga gaaggtcact atgagctgca gtccagtca gagtctttta     180 gctagtggca accaaaataa ctacttggcc tggcaccagc agaaaccagg acgatctcct     240
aaaatgctga atttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                            759

<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met
      protein)

<400> SEQUENCE: 78
atgaaggccc ccgctgtgct tgcacctggc atcctcgtgc tcctgtttac cttggtgcag      60
aggagcaatg gggagtgtaa agaggcacta gcaaagtccg agatgaatgt gaatatgaag     120
tatcagcttc ccaacttcac cgcggaaaca cccatccaga atgtcattct acatgagcat     180
cacattttcc ttggtgccac taactacatt tatgttttaa atgaggaaga ccttcagaag     240
```

-continued

```
gttgctgagt acaagactgg gcctgtgctg gaacacccag attgtttccc atgtcaggac      300
tgcagcagca aagccaattt atcaggaggt gtttggaaag ataacatcaa catggctcta      360
gttgtcgaca cctactatga tgatcaactc attagctgtg gcagcgtcaa cagagggacc      420
tgccagcgac atgtctttcc ccacaatcat actgctgaca tacagtcgga ggttcactgc      480
atattctccc cacagataga agagcccagc cagtgtcctg actgtgtggt gagcgccctg      540
ggagccaaag tcctttcatc tgtaaaggac cggttcatca acttctttgt aggcaatacc      600
ataaattctt cttatttccc agatcatcca ttgcattcga tatcagtgag aaggctaaag      660
gaaacgaaag atggttttat gttttttgacg gaccagtcct acattgatgt tttacctgag     720
ttcagagatt cttaccccat taagtatgtc catgcctttg aaagcaacaa ttttatttac      780
ttcttgacgg tccaaaggga aactctagat gctcagactt tcacacaag aataatcagg       840 ttctgttcca taaactctgg attgcattcc tacatggaaa tgcctctgga gtgtattctc      900
acagaaaaga gaaaaagag atccacaaag aaggaagtgt taatatact tcaggctgcg        960 tatgtcagca agcctggggc ccagcttgct agacaaatag gagccagcct gaatgatgac      1020
attcttttcg gggtgttcgc acaaagcaag ccagattctg ccgaaccaat ggatcgatct      1080
gccatgtgtg cattccctat caaatatgtc aacgacttct caacaagat cgtcaacaaa       1140 aacaatgtga gatgtctcca gcatttttac ggacccaatc atgagcactg ctttaatagg     1200
acacttctga gaaattcatc aggctgtgaa gcgcgccgtg atgaatatcg aacagagttt     1260
accacagctt tgcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaaatttga tttaagaaa     1800 actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg gaaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg ggaaaaacct gaattcagtt agtgtcccga gaatggtcat aaatgtgcat   2340
gaagcaggaa ggaactttac agtggcatgt caacatcgct ctaattcaga gataatctgt   2400
tgtaccactc cttccctgca acagctgaat ctgcaactcc cctgaaaac caaagccttt   2460 ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
```

```
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttcctgt ggctgaaaaa gagaaagcaa     2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca gtagccaaa ggcatgaaat atcttgcaag caaaagtttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctactatgt gaacgtaaaa     4080 tgtgtcgctc cgtatccttc tctgttgtca tcagaagata cgctgatga tgaggtggac      4140 acacgaccag cctccttctg ggagacatca                                      4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

```
Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80
```

```
Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80
```

-continued

```
Tyr Thr Leu Val Ile Thr Gly Lys Lys Ile Thr Lys Ile Pro Leu Asn
1               5                   10                  15
Gly Leu Gly Cys Arg His Phe Gln Ser Cys Ser Gln Cys Leu Ser Ala
            20                  25                  30
Pro Pro Phe Val Gln Cys Gly Trp Cys His Asp Lys Cys Val Arg Ser
            35                  40                  45
Glu Glu Cys Leu Ser Gly Thr Trp Thr Gln Gln Ile Cys Leu Pro Ala
50                  55                  60
Ile Tyr Lys Val Phe Pro Asn Ser Ala Pro Leu Glu Gly Gly Thr Arg
65                  70                  75                  80
Leu Thr Ile Cys Gly Trp Asp Phe Gly Phe Arg Arg Asn Asn Lys Phe
                85                  90                  95
Asp Leu Lys Lys Thr Arg Val Leu Leu Gly Asn Glu Ser Cys Thr Leu
                100                 105                 110
Thr Leu Ser Glu Ser Thr Met Asn Thr Leu Lys Cys Thr Val Gly Pro
            115                 120                 125
Ala Met Asn Lys His Phe Asn Met Ser Ile Ile Ser Asn Gly His
            130                 135                 140
Gly Thr Thr Gln Tyr Ser Thr Phe Ser Tyr Val Asp Pro Val Ile Thr
145                 150                 155                 160
Ser Ile Ser Pro Lys Tyr Gly Pro Met Ala Gly Gly Thr Leu Leu Thr
                165                 170                 175
Leu Thr Gly Asn Tyr Leu Asn Ser Gly Asn Ser Arg His Ile Ser Ile
                180                 185                 190
Gly Gly Lys Thr Cys Thr Leu Lys Ser Val Ser Asn Ser Ile Leu Glu
            195                 200                 205
Cys Tyr Thr Pro Ala Gln Thr Ile Ser Thr Glu Phe Ala Val Lys Leu
210                 215                 220
Lys Ile Asp Leu Ala Asn Arg Glu Thr Ser Ile Phe Ser Tyr Arg Glu
225                 230                 235                 240
Asp Pro Ile Val Tyr Glu Ile His Pro Thr Lys Ser Phe Ile Ser Thr
                245                 250                 255
Trp Trp Lys Glu Pro Leu Asn Ile Val Ser Phe Leu Phe Cys Phe Ala
            260                 265                 270
Ser Gly Gly Ser Thr Ile Thr Gly Val Gly Lys Asn Leu Asn Ser Val
            275                 280                 285
Ser Val Pro Arg Met Val Ile Asn Val His Glu Ala Gly Arg Asn Phe
            290                 295                 300
Thr Val Ala Cys Gln His Arg Ser Asn Ser Glu Ile Ile Cys Cys Thr
305                 310                 315                 320
Thr Pro Ser Leu Gln Gln Leu Asn Leu Gln Leu Pro Leu Lys Thr Lys
                325                 330                 335
Ala Phe Phe Met Leu Asp Gly Ile Leu Ser Lys Tyr Phe Asp Leu Ile
                340                 345                 350
Tyr Val His Asn Pro Val Phe Lys Pro Phe Glu Lys Pro Val Met Ile
                355                 360                 365
Ser Met Gly Asn Glu Asn Val Leu Glu Ile Lys Gly Asn Asp Ile Asp
370                 375                 380
Pro Glu Ala Val Lys Gly Glu Val Leu Lys Val Gly Asn Lys Ser Cys
385                 390                 395                 400
Glu Asn Ile His Leu His Ser Glu Ala Val Leu Cys Thr Val Pro Asn
                405                 410                 415
Asp Leu Leu Lys Leu Asn Ser Glu Leu Asn Ile Glu Trp Lys Gln Ala
```

```
                   420                 425                 430
Ile Ser Ser Thr Val Leu Gly Lys Val Ile Val Gln Pro Asp Gln Asn
                435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
                20                  25                  30

Lys Ser Leu Asn Arg Ile Thr Asp Ile Gly Glu Val Ser Gln Phe Leu
            35                  40                  45

Thr Glu Gly Ile Ile Met Lys Asp Phe Ser His Pro Asn Val Leu Ser
50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
            290                 295                 300

Arg Pro Ala Ser Phe Trp Glu Thr Ser
305                 310
```

```
<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain
      of c-Met)

<400> SEQUENCE: 82
ctacatgagc atcacatttt ccttggtgcc actaactaca tttatgtttt aaatgaggaa       60
gaccttcaga aggttgctga gtacaagact gggcctgtgc tggaacaccc agattgtttc      120
ccatgtcagg actgcagcag caaagccaat ttatcaggag gtgtttggaa agataacatc      180
aacatggctc tagttgtcga cacctactat gatgatcaac tcattagctg tggcagcgtc      240
aacagaggga cctgccagcg acatgtcttt ccccacaatc atactgctga catacagtcg      300
gaggttcact gcatattctc cccacagata gaagagccca gccagtgtcc tgactgtgtg      360
gtgagcgccc tgggagccaa agtcctttca tctgtaaagg accggttcat caacttcttt      420
gtaggcaata ccataaattc ttcttatttc ccagatcatc cattgcattc gatatcagtg      480
agaaggctaa aggaaacgaa agatggtttt atgtttttga cggaccagtc ctacattgat      540
gttttacctg agttcagaga ttcttacccc attaagtatg tccatgcctt tgaaagcaac      600
aattttattt acttcttgac ggtccaaagg gaaactctag atgctcagac ttttcacaca      660
agaataatca ggttctgttc cataaactct ggattgcatt cctacatgga aatgcctctg      720
gagtgtattc tcacagaaaa gagaaaaaag agatccacaa gaaggaagt gtttaatata      780 cttcaggctg cgtatgtcag caagcctggg gcccagcttg ctagacaaat aggagccagc      840
ctgaatgatg acattctttt cggggtgttc gcacaaagca agccagattc tgccgaacca      900
atggatcgat ctgccatgtg tgcattccct atcaaatatg tcaacgactt cttcaacaag      960
atcgtcaaca aaaacaatgt gagatgtctc cagcattttt acggacccaa tcatgagcac     1020
tgctttaata ggacacttct gagaaattca tcaggctgtg aagcgcgccg tgatgaatat     1080
cgaacagagt ttaccacagc tttgcagcgc gttgacttat tcatgggtca attcagcgaa     1140
gtcctcttaa catctatatc caccttcatt aaaggagacc tcaccatagc taatcttggg     1200
acatcagagg gtcgcttcat gcaggttgtg gtttctcgat caggaccatc aaccctcat     1260 gtgaattttc tcctggactc ccatccagtg tctccagaag tgattgtgga gcatacatta     1320
aaccaaaatg gc                                                         1332

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT
      domain of c-Met)

<400> SEQUENCE: 83
tacacactgg ttatcactgg aagaagatc acgaagatcc cattgaatgg cttgggctgc      60
agacatttcc agtcctgcag tcaatgcctc tctgccccac cctttgttca gtgtggctgg     120
tgccacgaca aatgtgtgcg atcggaggaa tgcctgagcg gacatggac tcaacagatc      180 tgtctgcctg caatctacaa ggttttccca aatagtgcac cccttgaagg agggacaagg     240
ctgaccatat gtggctggga ctttggattt cggaggaata taaatttga tttaaagaaa     300 actagagttc tccttggaaa tgagagctgc accttgactt aagtgagag cacgatgaat     360
```

```
acattgaaat gcacagttgg tcctgccatg aataagcatt tcaatatgtc cataattatt      420
tcaaatggcc acgggacaac acaatacagt acattctcct atgtggatcc tgtaataaca      480
agtatttcgc cgaaatacgg tcctatggct ggtggcactt tacttacttt aactggaaat      540
tacctaaaca gtgggaattc tagacacatt tcaattggtg gaaaaacatg tacttttaaaa     600
agtgtgtcaa acagtattct tgaatgttat accccagccc aaaccatttc aactgagttt      660
gctgttaaat tgaaaattga cttagccaac cgagagacaa gcatcttcag ttaccgtgaa      720
gatcccattg tctatgaaat tcatccaacc aaatctttta ttagtggtgg gagcacaata      780
acaggtgttg ggaaaaacct gaattcagtt agtgtcccga gaatggtcat aaatgtgcat      840
gaagcaggaa ggaactttac agtggcatgt caacatcgct ctaattcaga gataatctgt      900
tgtaccactc cttccctgca acagctgaat ctgcaactcc ccctgaaaac caaagccttt      960
ttcatgttag atgggatcct ttccaaatac tttgatctca tttatgtaca taatcctgtg     1020
tttaagcctt ttgaaaagcc agtgatgatc tcaatgggca atgaaaatgt actggaaatt     1080
aagggaaatg atattgaccc tgaagcagtt aaaggtgaag tgttaaaagt tggaaataag     1140
agctgtgaga atatacactt acattctgaa gccgttttat gcacggtccc caatgacctg     1200
ctgaaattga acagcgagct aaatatagag tggaagcaag caatttcttc aaccgtcctt     1260
ggaaaagtaa tagttcaacc agatcagaat ttcacagga                            1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain of c-Met)

<400> SEQUENCE: 84

```
gtgcatttca atgaagtcat aggaagaggg cattttggtt gtgtatatca tgggactttg       60
ttggacaatg atggcaagaa aattcactgt gctgtgaaat ccttgaacag aatcactgac      120
ataggagaag tttcccaatt tctgaccgag ggaatcatca tgaaagattt tagtcatccc      180
aatgtcctct cgctcctggg aatctgcctg cgaagtgaag ggtctccgct ggtggtccta      240
ccatacatga acatggaga tcttcgaaat tcattcgaa atgagactca taatccaact      300
gtaaaagatc ttattggctt tggtcttcaa gtagccaaag catgaaaata tcttgcaagc      360
aaaaagtttg tccacagaga cttggctgca agaaactgta tgctggatga aaaattcaca      420
gtcaaggttg ctgattttgg tcttgccaga gacatgtatg ataaagaata ctatagtgta      480
cacaacaaaa caggtgcaaa gctgccagtg aagtggatgg ctttggaaag tctgcaaact      540
caaaagttta ccaccaagtc agatgtgtgg tcctttggcg tgctcctctg ggagctgatg      600
acaagaggag ccccaccttta tcctgacgta aacacctttg atataactgt ttacttgttg      660
caagggagaa gactcctaca acccgaatac tgcccagacc ccttatatga agtaatgcta      720
aaatgctggc accctaaagc cgaaatgcgc ccatcctttt ctgaactggt gtcccggata      780
tcagcgatct tctctacttt cattggggag cactatgtcc atgtgaacgc tacttatgtg      840
aacgtaaaat gtgtcgctcc gtatccttct ctgttgtcat cagaagataa cgctgatgat      900
gaggtggaca cacgaccagc ctccttctgg gagacatca                             939
```

<210> SEQ ID NO 85
<211> LENGTH: 13
<212> TYPE: PRT

<213> ORGANISM: Artificial Sequence
<220> FEATURE:
<223> OTHER INFORMATION: Synthetic (heavy chain CDR3 of anti-c-Met antibody)

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met antibody)

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of monoclonal antibody AbF46)

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic (light chain variable region of anti-c-Met antibody)

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

```
Ser Pro Lys Met Leu Ile Ile Trp Ala Ser Thr Arg Val Ser Gly Val
    50              55                  60
Pro Asp Arg Phe Ile Gly Ser Gly Ser Gly Thr Asp Phe Thr Leu Thr
65              70                  75                  80
Ile Asn Ser Val Gln Ala Glu Asp Leu Ala Val Tyr Tyr Cys Gln Gln
                85                  90                  95
Ser Tyr Ser Ala Pro Leu Thr Phe Gly Ala Gly Thr Lys Leu Glu Leu
            100                 105                 110
Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 89

Gln Gln Ser Tyr Ser Ala Pro Leu Thr Phe Gly Ala Gly Thr Lys Leu
1               5                   10                  15
Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH1)

<400> SEQUENCE: 90

Glu Val Lys Leu Val Glu Ser Gly Gly Gly Leu Val Gln Pro Gly Gly
1               5                   10                  15
Ser Leu Arg Leu Ser Cys Ala Thr Ser Gly Phe Thr Phe Thr Asp Tyr
            20                  25                  30
Tyr Met Ser Trp Val Arg Gln Pro Pro Gly Lys Gly Leu Glu Trp Leu
        35                  40                  45
Gly Phe Ile Arg Asn Lys Ala Asn Gly Tyr Thr Thr Glu Tyr Ser Ala
    50                  55                  60
Ser Val Lys Gly Arg Phe Thr Ile Ser Arg Asp Asn Ser Lys Ser Thr
65              70                  75                  80
Leu Tyr Leu Gln Met Asn Ser Leu Arg Ala Glu Asp Ser Ala Thr Tyr
                85                  90                  95
Tyr Cys Ala Arg Asp Asn Trp Phe Ala Tyr Trp Gly Gln Gly Thr Leu
            100                 105                 110
Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH2)

<400> SEQUENCE: 91

Glu Val Lys Leu Val Glu Ser Gly Gly Gly Leu Val Gln Pro Gly Gly
1               5                   10                  15
```

```
Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH3)

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60
```

```
Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
                100                 105                 110

Val Thr Val Ser Ser
            115

<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH5)

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
             35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
                100                 105                 110

Val Thr Val Ser Ser
            115

<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
                100                 105                 110
```

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of
      AT-Vk1)

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of
      AT-Vk2)

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of
      AT-Vk3)

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of AT-Vk4)

<400> SEQUENCE: 99

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 100
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

```
Glu Pro Ser Cys Asp Lys His Cys Cys Pro Pro Cys Pro
1               5                   10
```

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

```
<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

Lys Ser Ser Gln Ser Leu Leu Ala Trp Gly Asn Gln Asn Asn Tyr Leu
1               5                   10                  15
Ala

<210> SEQ ID NO 107
<211> LENGTH: 114
<212> TYPE: PRT
<213> ORGANISM: Artificial Sequence
<220> FEATURE:
```

<223> OTHER INFORMATION: Synthetic (amino acid sequence of light chain
      variable region of antibody L3-11Y)

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic (amino acid sequence of light chain
      of antibody L3-11Y)

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys

<210> SEQ ID NO 109
<211> LENGTH: 120
<212> TYPE: PRT
<213> ORGANISM: Artificial Sequence
<220> FEATURE:
<223> OTHER INFORMATION: Synthetic (heavy-chain variable region of
      anti-EGFR antibody)

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 110
<211> LENGTH: 360
<212> TYPE: DNA
<213> ORGANISM: Artificial Sequence
<220> FEATURE:
<223> OTHER INFORMATION: Synthetic (DNA encoding heavy-chain variable
      region of SEQ ID NO. 109)

<400> SEQUENCE: 110
caggtgcagc tggtgcagtc tggggctgag gtgaagaagc ctgggtcctc ggtgaaggtc      60
tcctgcaagg cctctggttt cacattcact gactacaaga tacactgggt gcgacaggcc     120
cctggacaag ggctcgagtg gatgggatat ttcaacccta acagcggtta tagtacctac     180
gcacagaagt tccagggcag ggtcaccatt accgcggaca aatccacgag cacagcctac     240
atggagctga gcagcctgag atctgaggac acggccgtgt attactgtgc gagactatcc     300
ccaggcggtt actatgttat ggatgcctgg ggccaaggga ccaccgtgac cgtctcctca     360

<210> SEQ ID NO 111
<211> LENGTH: 108
<212> TYPE: PRT
<213> ORGANISM: Artificial Sequence
<220> FEATURE:
<223> OTHER INFORMATION: Synthetic (light-chain variable region of
      anti-EGFR antibody)

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

```
Tyr Asn Thr Asn Asn Leu Gln Thr Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Phe Pro Thr
                 85                  90                  95

Phe Gly Gln Gly Thr Lys Leu Glu Ile Lys Arg Thr
            100                 105
```

<210> SEQ ID NO 112
<211> LENGTH: 324
<212> TYPE: DNA
<213> ORGANISM: Artificial Sequence
<220> FEATURE:
<223> OTHER INFORMATION: Synthetic (DNA encoding light-chain variable
      region of SEQ ID NO. 111)

<400> SEQUENCE: 112

```
gatatccaga tgacccagtc tccatcctcc ctgtctgcat ctgtcggaga ccgggtcacc      60
atcacctgcc gggcaagtca gggcattaac aattacttaa attggtacca gcagaagcca     120
gggaaagccc ctaagcgcct gatctataat accaacaact tgcagacagg cgtcccatca     180
aggttcagcg gcagtggatc cgggacagaa ttcactctca ccatcagcag cctgcagcct     240
gaagattttg ccacctatta ctgcttgcag cataatagtt ttcccacgtt tggccagggc     300
accaagctcg agatcaagcg tacg                                            324
```

<210> SEQ ID NO 113
<211> LENGTH: 120
<212> TYPE: PRT
<213> ORGANISM: Artificial Sequence
<220> FEATURE:
<223> OTHER INFORMATION: Synthetic (heavy-chain variable region of
      anti-EGFR antibody (modified))

<400> SEQUENCE: 113

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Thr Phe Thr Asp Tyr
             20                  25                  30

Lys Ile His Trp Val Arg Gln Ala Pro Gly Gln Cys Leu Glu Trp Met
         35                  40                  45

Gly Tyr Ile Asn Pro Asn Ser Gly Tyr Ser Thr Tyr Ala Ser Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120
```

<210> SEQ ID NO 114
<211> LENGTH: 108
<212> TYPE: PRT
<213> ORGANISM: Artificial Sequence
<220> FEATURE:
<223> OTHER INFORMATION: Synthetic (light-chain variable region of
      anti-EGFR antibody (modified))

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Glu Ala Thr Tyr Tyr Cys Leu Gln His Asn Ser Phe Pro Thr
                85                  90                  95

Phe Gly Gln Gly Thr Lys Leu Glu Ile Lys Arg Thr
            100                 105

<210> SEQ ID NO 115
<211> LENGTH: 120
<212> TYPE: PRT
<213> ORGANISM: Artificial Sequence
<220> FEATURE:
<223> OTHER INFORMATION: Synthetic (heavy chain variable region of
      anti-Her2 antibody)

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 116
<211> LENGTH: 360
<212> TYPE: DNA
<213> ORGANISM: Artificial Sequence
<220> FEATURE:
<223> OTHER INFORMATION: Synthetic (DNA encoding heavy chain variable
      region of anti-Her2 antibody)

<400> SEQUENCE: 116
gaagttcagc tggtggagtc tggcggtggc ctggtgcagc caggggggctc actccgtttg     60 tcctgtgcag cttctggctt caacattaaa gacacctata tacactgggt gcgtcaggcc    120
ccgggtaagg gcctggaatg ggttgcaagg atttatccta cgaatggtta tactagatat    180
gccgatagcg tcaagggccg tttcactata agcgcagaca catccaaaaa cacagcctac    240
ctgcagatga acagcctgcg tgctgaggac actgccgtct attattgttc tagatgggga    300

```
ggggacggct tctatgctat ggactactgg ggtcaaggaa ccctggtcac cgtctcctcg    360
```

<210> SEQ ID NO 117
<211> LENGTH: 108
<212> TYPE: PRT
<213> ORGANISM: Artificial Sequence
<220> FEATURE:
<223> OTHER INFORMATION: Synthetic (light chain variable region of
      anti-Her2 antibody)

<400> SEQUENCE: 117

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105
```

<210> SEQ ID NO 118
<211> LENGTH: 324
<212> TYPE: DNA
<213> ORGANISM: Artificial Sequence
<220> FEATURE:
<223> OTHER INFORMATION: Synthetic (DNA encoding light chain variable
      region of anti-Her2 antibody)

<400> SEQUENCE: 118

```
gatatccaga tgacccagtc cccgagctcc ctgtccgcct ctgtgggcga tagggtcacc    60
atcacctgcc gtgccagtca ggatgtgaat actgctgtag cctggtatca acagaaacca   120
ggaaaagctc cgaaactact gatttactcg gcatccttcc tctactctgg agtcccttct   180
cgcttctctg gttccagatc tgggacggat ttcactctga ccatcagcag tctgcagccg   240
gaagacttcg caacttatta ctgtcagcaa cattatacta ctcctcccac gttcggacag   300
ggtaccaagg tggagatcaa acga                                          324
```

<210> SEQ ID NO 119
<211> LENGTH: 24
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 119

```
Phe Ala Pro Gln Ile Glu Glu Pro Ser Gln Cys Pro Asp Cys Val Val
1               5                   10                  15

Ser Ala Leu Gly Ala Lys Val Leu
            20
```

<210> SEQ ID NO 120
<211> LENGTH: 11
<212> TYPE: PRT

-continued

```
<213> ORGANISM: Artificial Sequence
<220> FEATURE:
<223> OTHER INFORMATION: Synthetic (Synthesized peptide sequence for
      epitope mapping)

<400> SEQUENCE: 120

Cys Ser Pro Gln Ile Glu Glu Pro Ser Gln Cys
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 121

Cys Pro Gln Ile Glu Glu Pro Ser Gln Ala Cys
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 122

Cys Gln Ile Glu Glu Pro Ser Gln Ala Pro Cys
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 123

Cys Ile Glu Glu Pro Ser Gln Ala Pro Asp Cys
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 124

Cys Glu Glu Pro Ser Gln Ala Pro Asp Ala Cys
1               5                   10

<210> SEQ ID NO 125
<211> LENGTH: 5
<212> TYPE: PRT
<213> ORGANISM: Artificial Sequence
<220> FEATURE:
<223> OTHER INFORMATION: Synthetic (core peptide sequence for epitope
      mapping)

<400> SEQUENCE: 125

Glu Asp Pro Ser Gln
1               5
```

```
<210> SEQ ID NO 126
<211> LENGTH: 24
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 126

Phe Ser Pro Gln Ile Glu Asp Pro Ser Gln Cys Pro Asp Cys Val Val
1               5                   10                  15

Ser Ala Leu Gly Ala Lys Val Leu
            20

<210> SEQ ID NO 127
<211> LENGTH: 11
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 127

Cys Ser Pro Gln Ile Glu Asp Pro Ser Gln Cys
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 128

Cys Pro Gln Ile Glu Asp Pro Ser Gln Ala Cys
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 129

Cys Gln Ile Glu Asp Pro Ser Gln Ala Pro Cys
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic (Synthesized peptide sequence for
      epitope mapping)

<400> SEQUENCE: 130

Cys Ile Glu Asp Pro Ser Gln Ala Pro Asp Cys
1               5                   10

<210> SEQ ID NO 131
<211> LENGTH: 11
<212> TYPE: PRT
<213> ORGANISM: Artificial Sequence
```

```
<220> FEATURE:
<223> OTHER INFORMATION: Synthetic (Synthesized peptide sequence for
      epitope mapping)

<400> SEQUENCE: 131

Cys Glu Asp Pro Ser Gln Ala Pro Asp Ala Cys
1               5                   10

<210> SEQ ID NO 132
<211> LENGTH: 5
<212> TYPE: PRT
<213> ORGANISM: Artificial Sequence
<220> FEATURE:
<223> OTHER INFORMATION: Synthetic (Epitope variant)

<400> SEQUENCE: 132

Ala Ala Ala Ala Ala
1               5

<210> SEQ ID NO 133
<211> LENGTH: 5
<212> TYPE: PRT
<213> ORGANISM: Artificial Sequence
<220> FEATURE:
<223> OTHER INFORMATION: Synthetic (Epitope variant)

<400> SEQUENCE: 133

Ala Glu Pro Ser Gln
1               5

<210> SEQ ID NO 134
<211> LENGTH: 5
<212> TYPE: PRT
<213> ORGANISM: Artificial Sequence
<220> FEATURE:
<223> OTHER INFORMATION: Synthetic (Epitope variant)

<400> SEQUENCE: 134

Glu Ala Pro Ser Gln
1               5

<210> SEQ ID NO 135
<211> LENGTH: 5
<212> TYPE: PRT
<213> ORGANISM: Artificial Sequence
<220> FEATURE:
<223> OTHER INFORMATION: Synthetic (Epitope variant)

<400> SEQUENCE: 135

Glu Glu Ala Ser Gln
1               5

<210> SEQ ID NO 136
<211> LENGTH: 5
<212> TYPE: PRT
<213> ORGANISM: Artificial Sequence
<220> FEATURE:
<223> OTHER INFORMATION: Synthetic (Epitope variant)

<400> SEQUENCE: 136

Glu Glu Pro Ala Gln
1               5

<210> SEQ ID NO 137
<211> LENGTH: 5
<212> TYPE: PRT
<213> ORGANISM: Artificial Sequence
```

```
<220> FEATURE:
<223> OTHER INFORMATION: Synthetic (Epitope variant)

<400> SEQUENCE: 137

Glu Glu Pro Ser Ala
1               5

<210> SEQ ID NO 138
<211> LENGTH: 114
<212> TYPE: PRT
<213> ORGANISM: Artificial Sequence
<220> FEATURE:
<223> OTHER INFORMATION: light chain variable region of anti c-Met
      antibody

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

METHOD OF TARGET MEMBRANE PROTEIN DEPLETION

CROSS-REFERENCE TO RELATED APPLICATIONS

This application claims the benefit of Korean Patent Application No. 10-2013-0061282, filed on May 29, 2013 with the Korean Intellectual Property Office, and Korean Patent Application No. 10-2014-0063899 filed on May 27, 2014, with the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 150,638 Bytes ASCII (Text) file named "716186_ST25_revised," created on Aug. 27, 2015.

BACKGROUND OF THE INVENTION

1. Field of the Invention

Provided are a composition for target membrane protein depletion, including a dual binding molecule including a first binding domain and a second binding domain which interact with a driver membrane protein and a target membrane protein, respectively, a pharmaceutical composition for the treatment and prevention of cancer, including the same as an active ingredient, and a method of target membrane protein depletion using the same.

2. Description of the Related Art

Membrane proteins are attached to, or associated with the membrane of a cell or an organelle, and perform their own characteristic functions according to the position thereof. Investigation into the functions of membrane proteins relies predominately on the use of siRNA to interfere with the expression of proteins of interest. However, there is a limitation to studying the functions of membrane proteins by the interference of protein expression with siRNA.

A more advantageous approach to identifying the function of a membrane protein is to remove the protein after it is normally expressed and located in the membrane. For example, 58 different receptor tyrosine kinases (RTKs), known as cancer cell-related membrane proteins, share a fairly common structure. These RTK proteins form homodimers or heterodimers depending on the binding of ligands thereto, and participate in signaling pathways through interaction with various membrane or intracellular proteins, resulting in various actions including cell proliferation, differentiation, migration, survival, attachment, and metabolism. That is to say, a membrane protein performs its own function, for example, transduces signals from the extracellular matrix into the cytoplasm only after it is normally expressed and located in the membrane.

As described above, the functions of membrane proteins are investigated predominantly by use of siRNAs, but with a limitation imposed thereto, and since the characteristic functions of membrane proteins are greatly affected by their locations in the cell, it is preferred and required that membrane proteins be depleted after they are normally expressed and located in membranes. Particularly, a method of target membrane protein depletion can be universally employed like siRNA technology if it allows for deletion of target-specific proteins on a plasma membrane.

Therefore, a technique is needed for deleting normally expressed and located membrane proteins, including RTKs, which will be useful in the analysis of accurate membrane protein functions and the effective regulation of membrane proteins.

SUMMARY OF THE INVENTION

Provided herein is a method of target membrane protein depletion, the method comprising treating a cell with a dual binding molecule comprising a first binding domain which binds to a driver membrane protein and a second binding domain which binds to a target membrane protein, wherein the cell comprises a cell membrane, and the driver membrane protein and target membrane protein are associated with the cell membrane where the target membrane protein positions, and are internalized into the cell and degraded when the first binding domain of the dual binding molecule binds the driver membrane protein.

Also provided is a method of treating or preventing cancer in a subject comprising administering to the subject a dual binding molecule. In related aspects, a dual binding molecule is provided, as well as a pharmaceutical composition comprising the dual binding molecule.

BRIEF DESCRIPTION OF THE DRAWINGS

The patent or application file contains at least one drawing executed in color. Copies of this patent or patent application publication with color drawings will be provided by the Office upon request and payment of the necessary fee.

Figure 9:
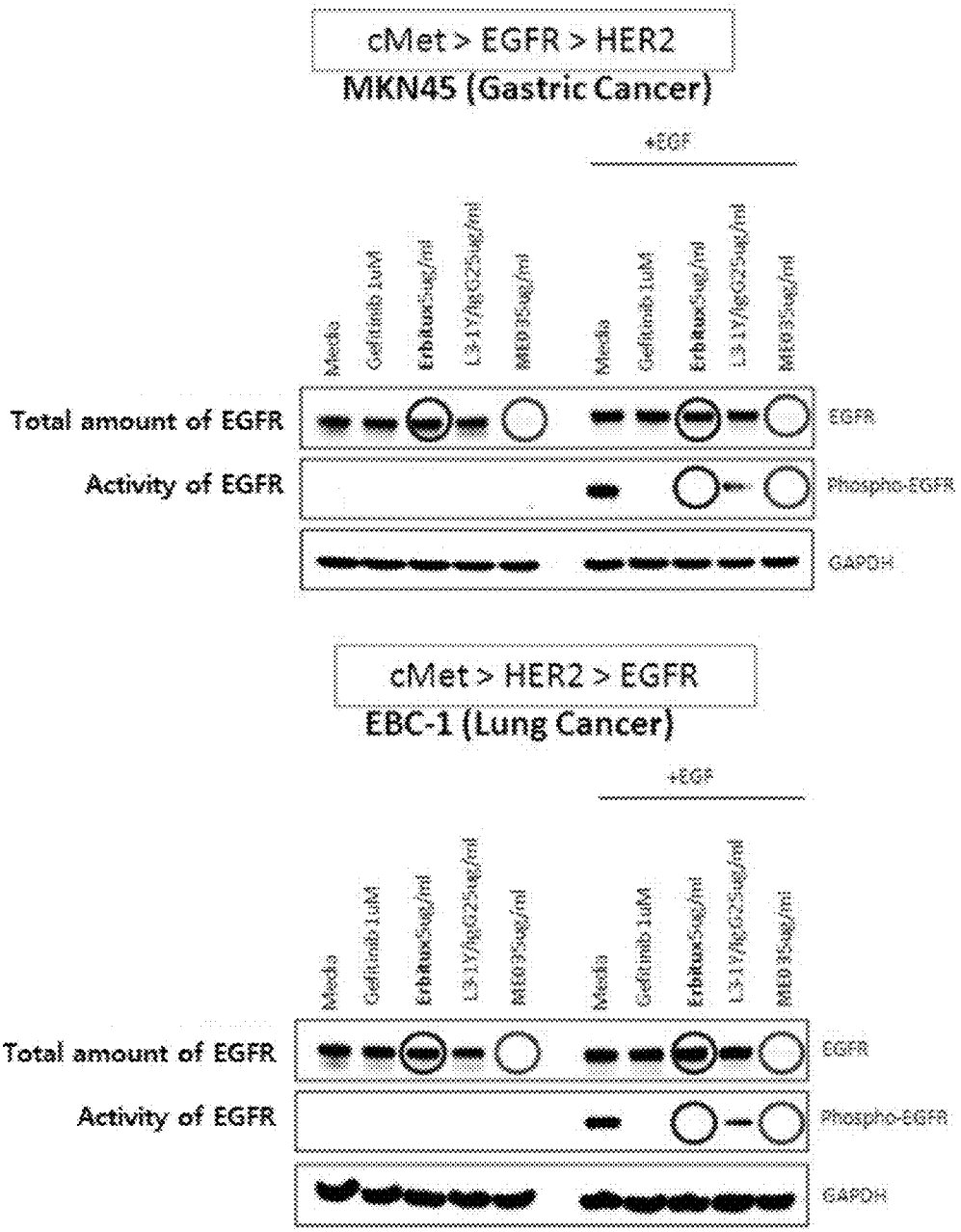

FIG. 9 shows a total level of EGFR and EGFR activity in MKN45 stomach cancer cells (upper panel) and EBC-1 lung cancer cells (lower panel) after treatment with the anti-c-Met/anti-EGFR bispecific antibody, as measured by Western blotting.

Figure 10:
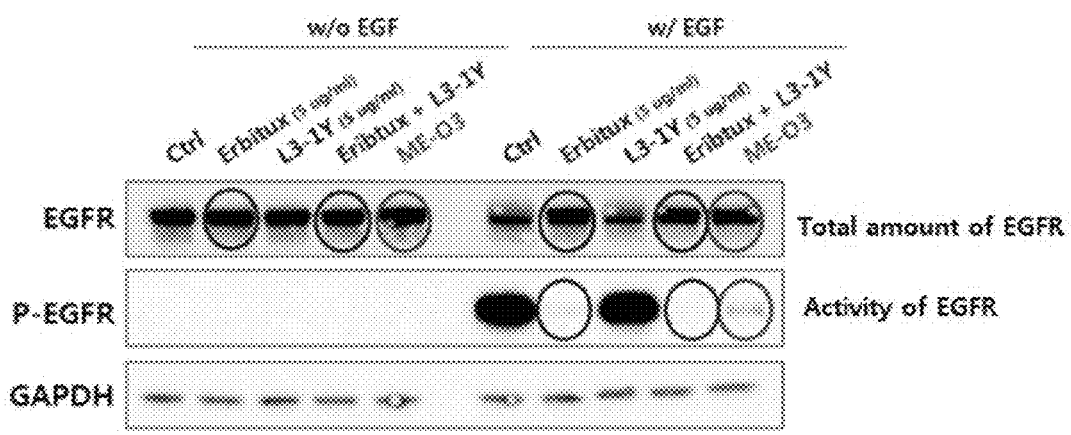

FIG. 10 shows a total level of EGFR and EGFR activity in A431 cancer cells with low expression level of c-Met after treatment with the anti-c-Met/anti-EGFR bispecific antibody, as measured by Western blotting.

Figure 11:
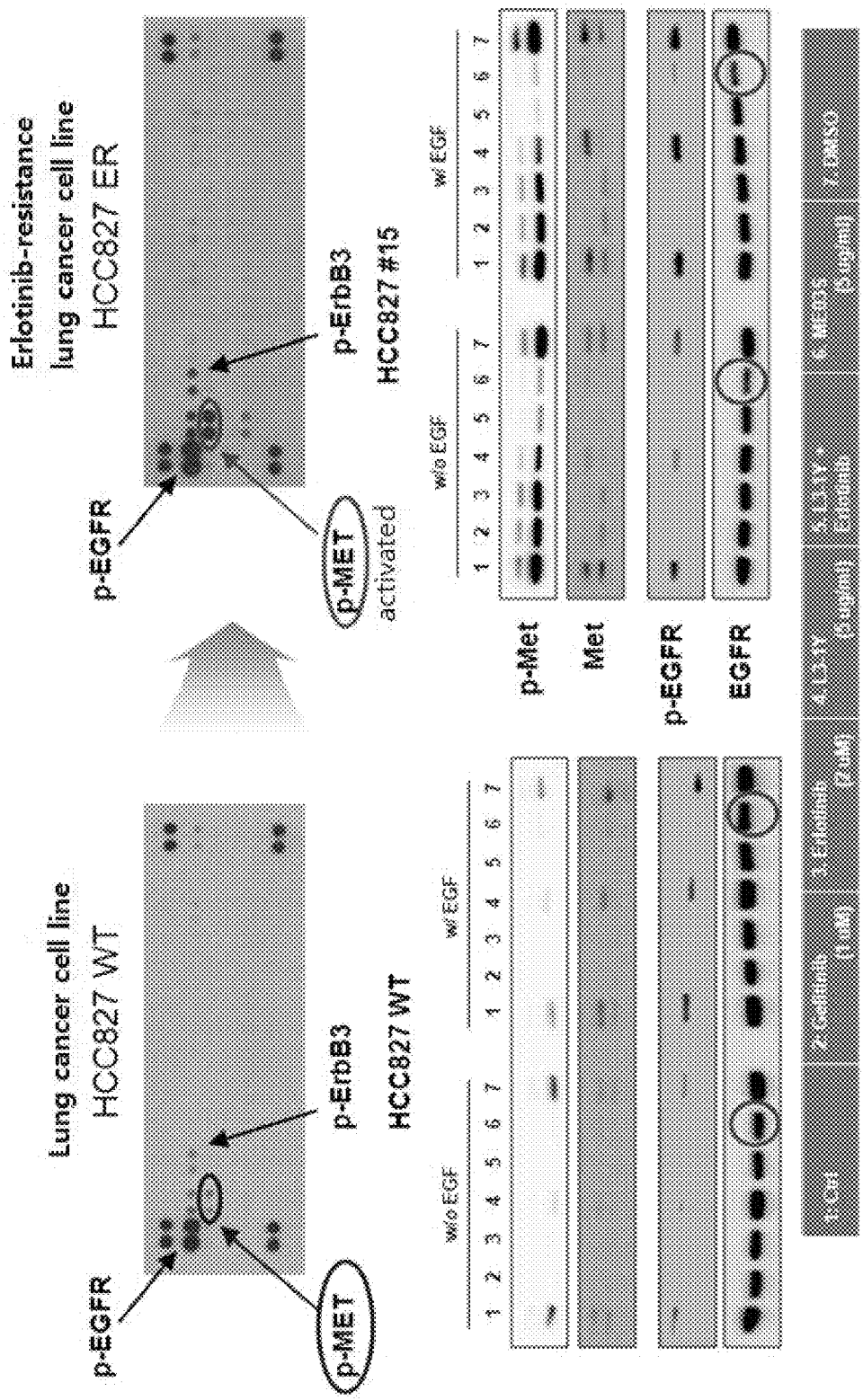

FIG. 11 shows the effect of c-Met on EGFR degradation in wild-type HCC827 lung cancer cells and HCC827 Erlotinib-resistant cells (HCC827 ER), as measured by Western blotting.

Figure 12:
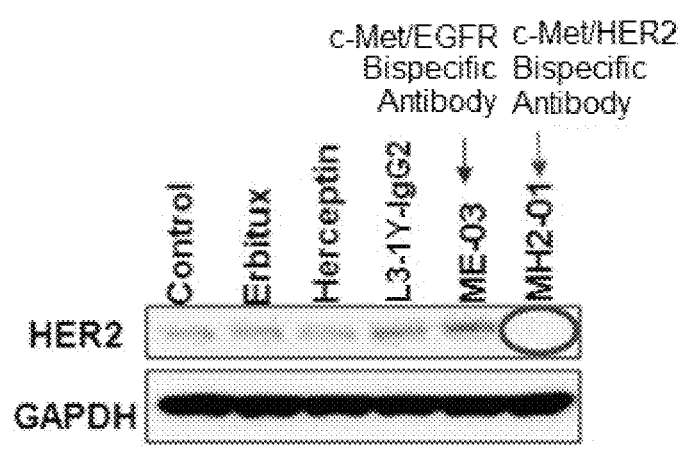

FIG. 12 shows HER2-specific degradation by the anti-c-Met/anti-Her2 bispecific antibody in MKN45 stomach cancer cells, as measured by Western blotting.

Figure 13:
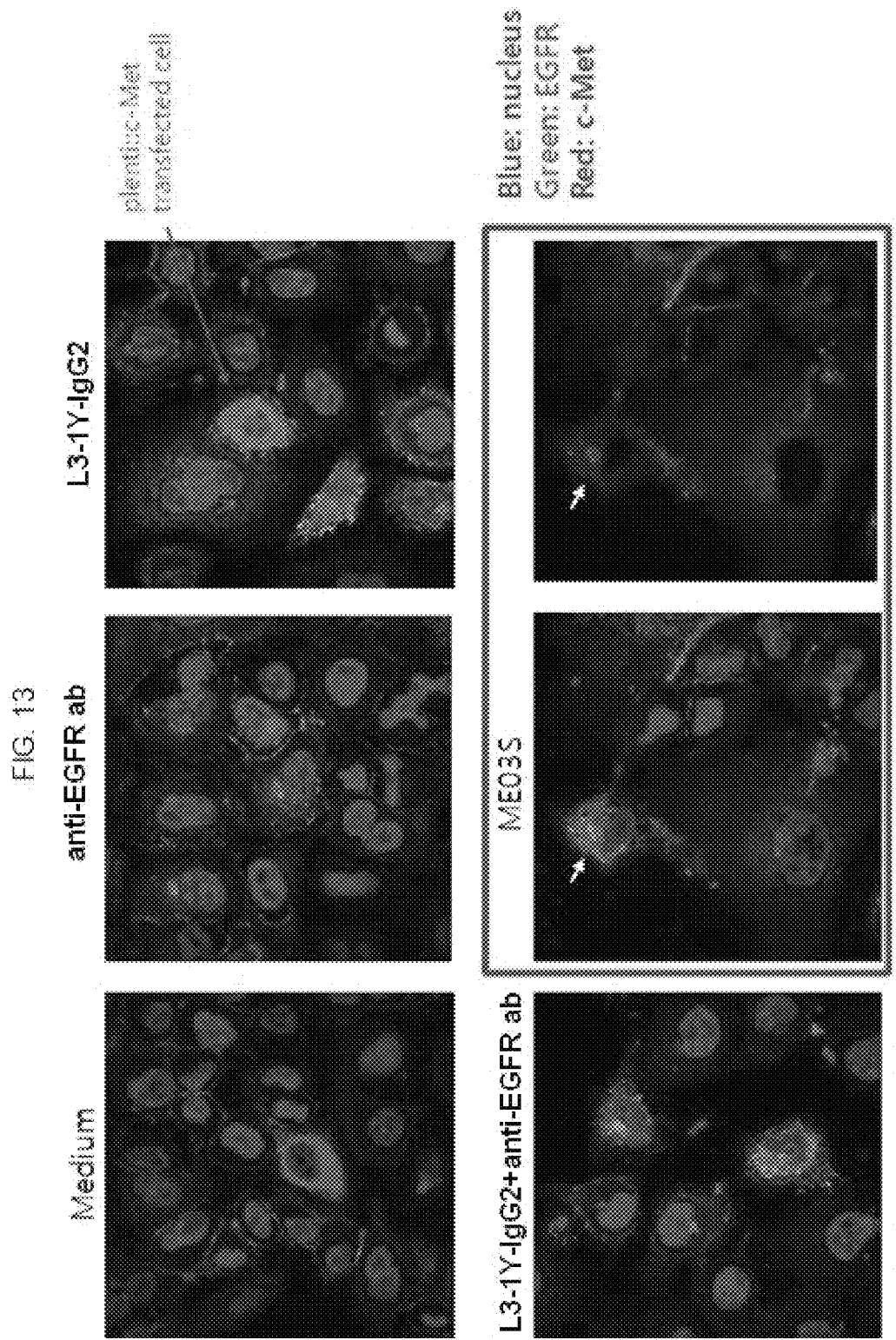

FIG. 13 shows fluorescent images illustrating the effect of c-Met on the anti-c-Met/anti-EGFR bispecific antibody-induced degradation of EGFR in A549 cancer cells with low expression level of c-Met, after overexpressing c-Met in the cells.

Figure 14:
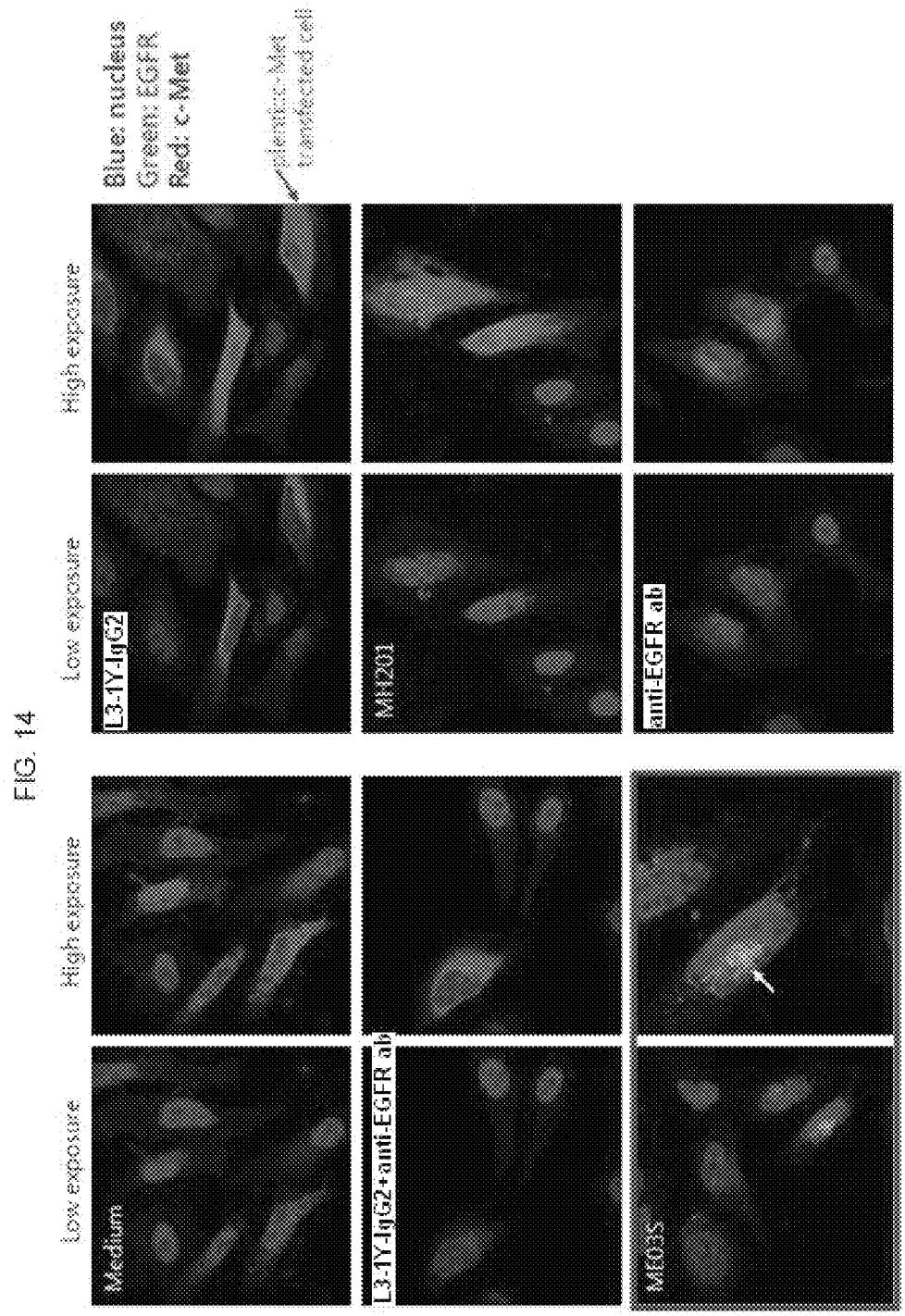

FIG. 14 shows fluorescent images illustrating the effect of c-Met on the anti-c-Met/anti-EFGR bispecific antibody-induced degradation of EGFR in HeLa cells with low expression level of c-Met, after overexpressing c-Met in the cells.

Figure 15:
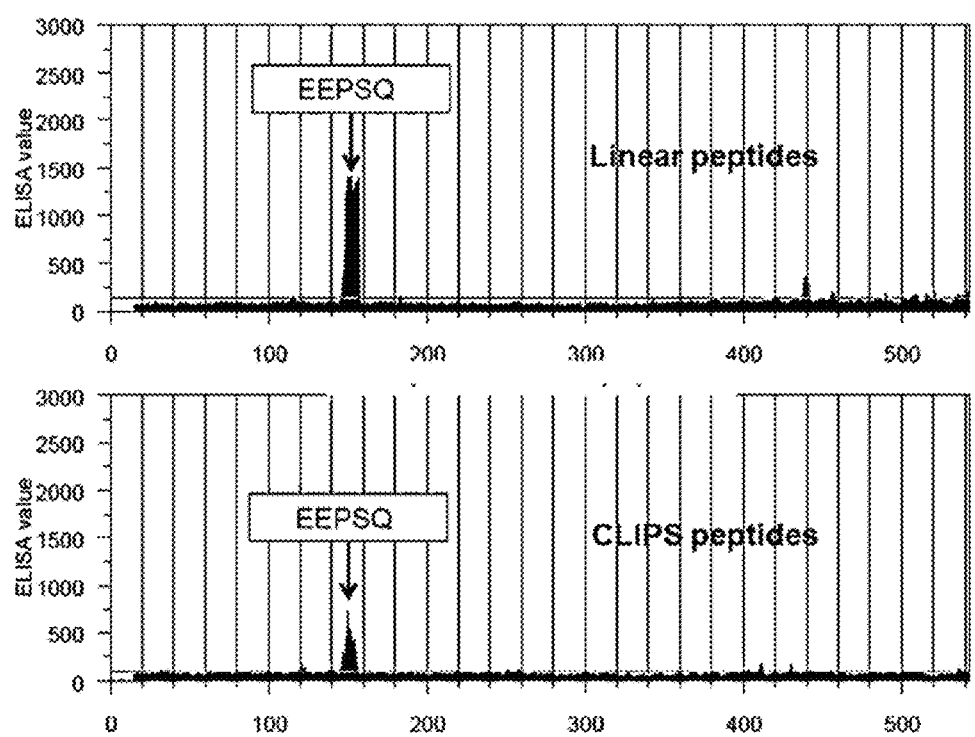

FIG. 15 includes graphs showing the results of ELISA for epitope mapping of huAbF46 antibody. In FIG. 15, "EEPSQ" corresponds to SEQ ID NO: 73.

FIGS. 16A-16B are schematic views of huAbF46 antibody, indicating the position of the epitope on SEMA domain of the antibody. In FIG. 16A, "EEPSQ" corresponds to SEQ ID NO: 73.

DETAILED DESCRIPTION OF THE INVENTION

One embodiment provides a composition for target-specific cell membrane depletion, including a dual binding molecule including a first binding domain binding to a driver membrane protein and a second binding domain binding to a target membrane protein.

The dual binding molecule simultaneously binds both a driver membrane protein and a target membrane protein through its first and second binding domains. Once bound with the dual binding molecule, the driver membrane protein is triggered to undergo endocytocis, with the consequent migration of the bound target membrane protein into the cell, and the proteins are eventually degraded inside the cells (see FIGS. 1 and 2).

Figure 1:
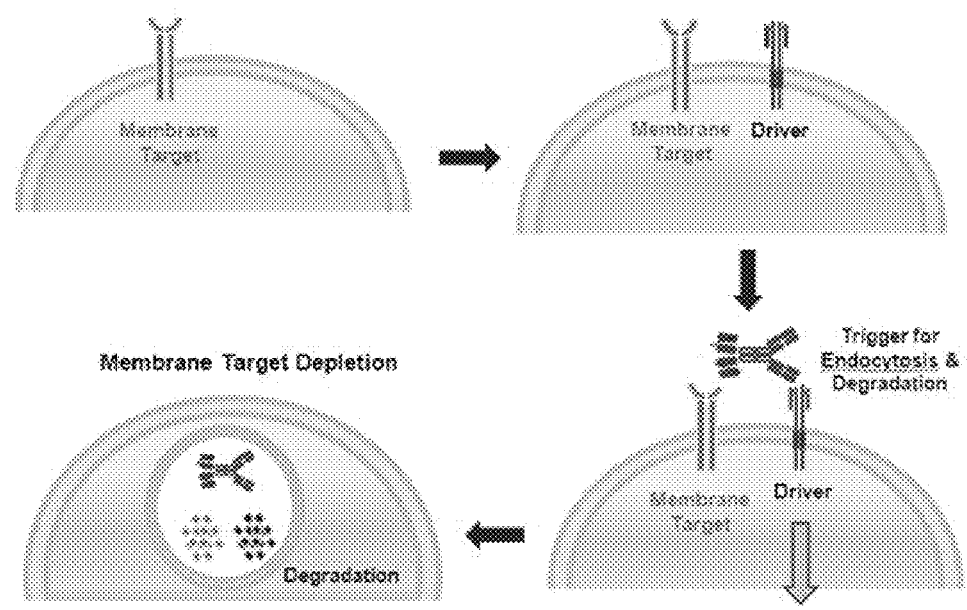
FIG. 1 is a schematic diagram illustrating a mechanism of target membrane protein depletion.

FIG. 1 presents schematic diagrams illustrating a technique of membrane protein depletion according to an embodiment. In FIG. 1, when a dual binding molecule capable of recognizing the target membrane protein and simultaneously binding to a driver membrane protein is applied to a cell containing both a target and a driver in the membrane, binding of the dual binding molecule serves as a trigger to initiate endocytosis and degradation.

Figure 2:
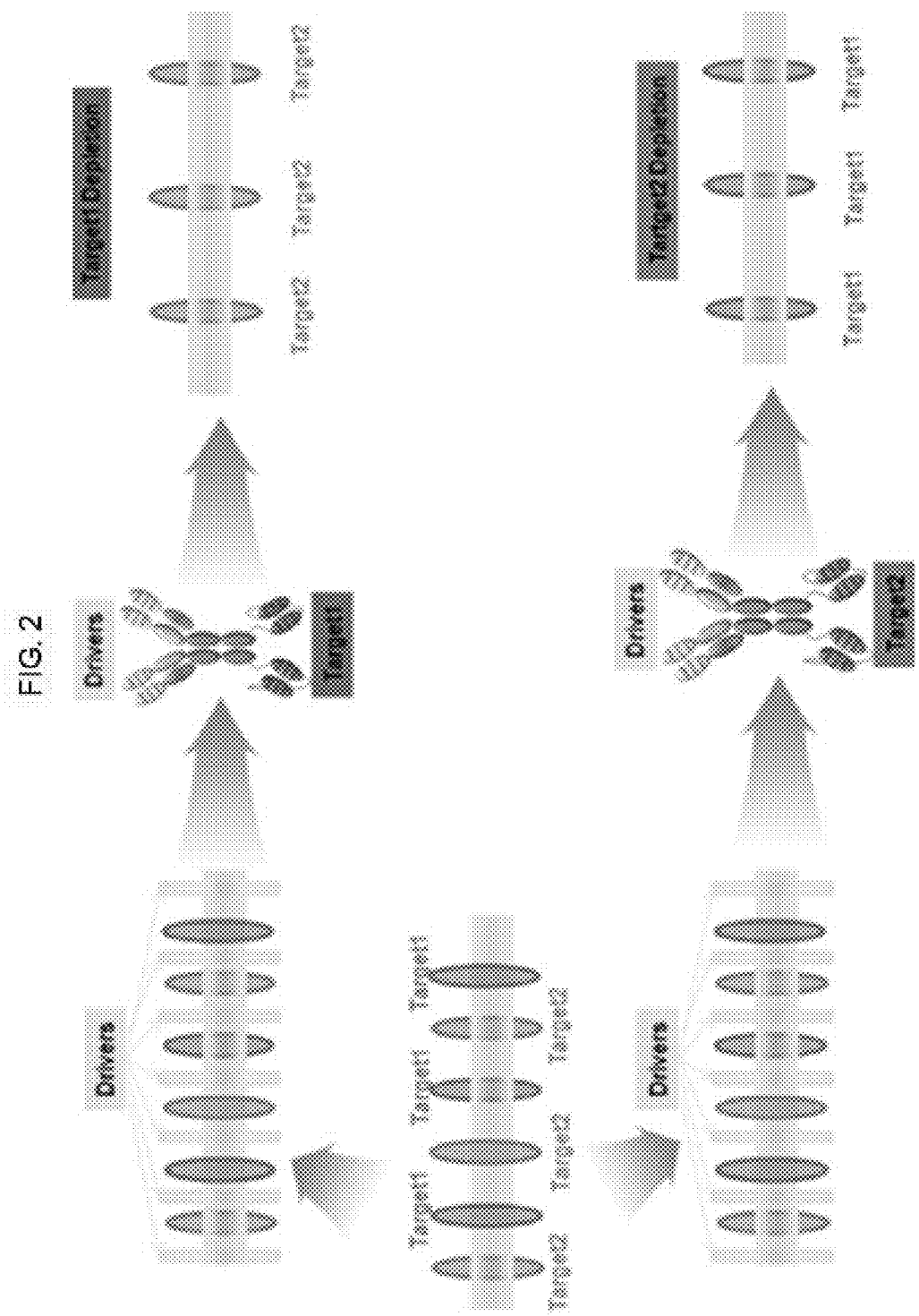
FIG. 2 is a schematic diagram illustrating target membrane protein depletion from plasma membranes.

FIG. 2 provides schematic diagrams illustrating the mechanism of target membrane protein depletion in a target specific manner according to an embodiment. Although a variety of proteins are present in a plasma membrane, the dual binding molecule is specific for a target without interacting with other membrane proteins, thus triggering the internalization and degradation of only the target protein with the driver protein.

The term "driver membrane protein," as used herein, refers to a protein serving to transport a target membrane protein into the cell via interaction with the dual binding molecule.

The driver membrane protein may be any protein that undergoes internalization by interaction (e.g., binding) with a ligand, antibody, or other protein or peptide. Similarly, the target membrane protein may be any proteins located on a cell membrane, that can be internalized when linked to the driver protein by way of a dual binding molecule. The driver and target protein may be independently selected from the group consisting of receptors, channel proteins, membrane enzymes, lipoproteins, integrins, various markers on cell surface, and the like. For example, the driver membrane protein and the target membrane protein may be independently selected from the group consisting of receptor tyrosine kinases (e.g., c-Met protein, c-Met protein mutants, EGFR, HER2, HER3, VEGFR, PDGFR, IGF1R, ephrin receptors, FGFR, etc.), Integrins, NMDA receptors, G-protein-coupled receptor (GPCR), transferrin receptors, low-density lipoprotein (LDL) receptors, clusters of differentiation or clusters of designation (CDs) (e.g., CD11a, CD20, CD3, CD33, CD44, CD59, CD73, CD152 (CTLA4), etc.), NTRK2 (neurotrophic tyrosine kinase), peripheral membrane proteins, tetraspanins (e.g., CD9, CD81, CD 151, CD63, CD37, CD53, NET1, NET2, NET4, NET5, NET6, TM4SF6, Tspan2, Tspan3, TM4B, etc.), and membrane targets for antibody drug conjugates (ADC) which could be internalized by antibody binding (Ref: 2013 Nature Reviews Drug Discovery 12:330, which is incorporated herein by reference) (e.g., CD22, CD 79b, CD22, GPNMB, CD19, CD56, CD138, PSMA, EGFR, CD74, TACSTD2, CEA, Folate receptor 1, CD37, Mucin16, ETB, STEAP1, CD70, SLC44A4, Nectin4, AGS-16, Guanylyl cyclase C, Mucin1, EGFRvIII, Mesothelin, etc.).

In one embodiment, the driver membrane protein may be any protein that can be internalized into a cell when its extracellular domain is bound with a ligand or an antibody. Alternatively, the driver membrane protein may be a mutant which is configured to undergo endocytosis upon interaction with a ligand or an antibody while the wild-type does not.

In another embodiment, the driver membrane protein may be a protein which is located on or introduced into the same membrane where the target membrane protein is positioned. The driver membrane protein is triggered to be internalized into a cell and degraded when the first binding domain of the dual binding molecule binds thereto. According to one embodiment, the driver membrane protein may be at least one selected from the group consisting of:

1) receptor tyrosine kinases (RTKs) that can be induced to undergo internalization by interaction with ligands, antibodies, non-antibody proteins, (e.g., c-Met protein, c-Met protein mutants, epidermal growth factor receptor (EGFR; ErbB1), HER2 (human epidermal growth factor receptor 2 protein; ErbB2), HER3 (human epidermal growth factor receptor 3 protein; ErbB3), platelet-derived growth factor receptors (PDGFR), vascular endothelial growth factors (VEGFR), insulin-like growth factor 1 receptor (IGF1R), ephrin receptors, fibroblast growth factor receptor (FGFR));

2) receptors that are induced to undergo internalization by interaction with ligands, antibodies, non-antibody proteins, (e.g., transferrin receptors, low-density lipoprotein (LDL) receptors, clusters of differentiation or clusters of designation (CD) (e.g., CD11a, CD20, CD3, CD33, CD44, CD59, CD73, CD152 (CTLA4)), NTRK2 (neurotrophic tyrosine kinase));

3) tetraspanins (e.g., CD9, CD81, CD 151, CD63, CD37, CD53, NET1, NET2, NET4, NET5, NET6, TM4SF6, Tspan2, Tspan3, TM4B); and 4) membrane targets for antibody drug conjugates (ADC) which could be internalized by antibody binding (Ref: 2013 Nature Reviews Drug Discovery 12:330) (e.g., CD22, CD 79b, CD22, GPNMB, CD19, CD56, CD138, PSMA, EGFR, CD74, TACSTD2, CEA, Folate receptor 1, CD37, Mucin16, ETB, STEAP1, CD70, SLC44A4, Nectin4, AGS-16, Guanylyl cyclase C, Mucin1, EGFRvIII, Mesothelin.).

In an embodiment, the driver membrane protein may be c-Met protein and the first binding domain of the dual binding molecule, which binds to a driver membrane protein, may binds to the amino sequence of SEQ ID NO: 73 (EEPSQ) ranging from position 143 to position 147 of SEMA domain (SEQ ID NO: 79) of c-Met protein.

The target membrane protein may be any kind of membrane protein irrespective of type, property and function. In addition, a membrane protein that is not triggered itself to be internalized in a cell may be within the scope of the target.

For example, the target membrane protein may be a receptor mediating cell signals related with abnormal cells, as in oncogenesis, or a channel protein. In one embodiment, the target membrane protein may be a therapeutic target of a disease related with abnormal cells, such as cancer.

As mentioned above, the target membrane protein may be any membrane protein, including integral proteins, such as G-protein-coupled receptors (GPCRs), receptor tyrosine kinases, etc., and peripheral membrane proteins. Particularly, it may be selected from the group consisting of microfilament-associated proteins, cell adhesion molecules, membrane enzymes, membrane receptors, carrier proteins, channel proteins, transport proteins, lipid-anchored proteins directing outward of cells, and a combination thereof. Any integral protein may be used as a target membrane protein if it is internalized by interaction with a ligand or an antibody as described above, in conjugation with the driver membrane protein. In one embodiment, the integral protein may be selected from the group consisting of receptor tyrosine kinases (RTKs), G-protein-coupled receptors (GPCR), and receptors (transferrin receptors, low-density lipoprotein (LDL) receptors, clusters of differentiation (clusters of designation; CD)), and a combination thereof. The target membrane protein may be one of the proteins which plays an important role in cellular functions, and is selected, inter alia, from the group consisting of epidermal growth factor receptor (EGFR), vascular endothelial growth factor receptor (VEGFR), HER2 protein (human epidermal growth factor receptor 2 protein), HER3 protein (human epidermal growth factor receptor 3 protein), and platelet-derived growth factor receptors (PDGFR).

As used herein, the term "c-Met protein" means a receptor tyrosine kinase that binds to a hepatocyte growth factor ligand. The c-Met protein may be originated from any species, for example, primate origin, such as human c-Met (e.g., NP_000236) and rhesus c-Met (e.g., Macaca mulatta, NP_001162100), or rodent origin, such as murine c-Met (e.g., NP_032617.2) and rat c-Met (e.g., NP_113705.1). The protein may include, for example, a polypeptide encoded by the nucleotide sequence identified as GenBank Accession Number NM_000245, or a protein including the amino acid sequence identified as GenBank Accession Number NP_000236, or the polypeptide or protein plus the extracellular domain thereof. The c-Met protein, known as a receptor tyrosine kinase, is implicated in various activities including oncogenesis, cancer metastasis, migration and infiltration of cancer cells, and angiogenesis.

Epidermal growth factor receptor (EGFR), HER2 (human epidermal growth factor receptor 2 protein), and HER3 (human Epidermal growth factor receptor 3 protein) are members of the HER family composed of four plasma membrane-bound receptor tyrosine kinases (RTKs), EGFR(HER1), HER2, HER3 and HER4.

EGFR, HER2, and HER3 are induced to homo- or heterodimerize with any of the four ErbB receptors when their extracellular domains are bound with a ligand, resulting in the autophosphorylation of tyrosine residues within the cytoplasmic domain of the receptors. EGFR autophosphorylation leads to downstream signaling networks including MAPK and PI3K/Akt activation, which, in turn, induces cell proliferation, angiogenesis and metastasis. Overexpression, or gene amplification, mutation or rearrangement of EGFR, HER2 and/or HER3 is frequently found in many different human malignant tumors, and is associated with poor prognosis and clinical outcome of cancer treatment. For this reason, EGFR, HER2, and/or HER3 are important targets for anticancer therapy.

EGFR, HER2, or HER3 may have originated from mammals such as primates (e.g., humans, monkeys) and rodents (e.g., mice and rats). For example, EGFR is a polypeptide including the amino acid sequence encoded by the nucleotide sequence (mRNA) identified as GenBank Accession Nos. JQ739160, JQ739161, JQ739162, JQ739163, JQ739164, JQ739165, JQ739166, JQ739167, NM_005228.3, NM_201284.1, NM_201282.1, or NM_201283.1. In one embodiment, HER2 may be a polypeptide encoded by the nucleotide sequence (mRNA) of GenBank Accession No. X03363.1 while HER3 may be a polypeptide encoded by the nucleotide sequence (mRNA) of GenBank Accession No. NM_001982.

Vascular endothelial cell growth factor receptors (VEGFRs) are present in the plasma membrane of cancer cells as well as normal cells, and mediate the VEGF-induced signaling of angiogenesis, which is necessary for the supply of nutrients to cancer cells. Overexpression of VEGFRs is responsible for an etiology of various diseases, inter alia, oncogenesis, and is implicated in poor treatment prognoses, such as invasion, metastasis, etc. Accordingly, VEGFR is an important target for anticancer therapy. A VEGFR may originate from a mammal including primates such as humans and monkeys, and rodents such as mice and rats. For example, VEGFR may be a polypeptide including the amino acid sequence encoded by the nucleotide sequence (mRNA) of GenBank Accession Number AF063657.2.

Platelet-derived growth factor receptors (PDGFRs) are cell surface tyrosine kinase receptors, and are implicated in the regulatory mechanism of cell proliferation, differentiation and growth, and the onset of various diseases including cancer. PDGFRs may originate from a mammal including primates such as humans and monkeys, and rodents such as mice and rats. For example, the PDGFR may be a polypeptide including the amino acid sequence encoded by the nucleotide sequence (mRNA) of GenBank Accession Nos. NM_006206.4 (PDGFR-A), NM_002609.3 (PDGFR-B), or NM_016205.2 (PDGFR-C). The insulin-like growth factor 1 receptor (IGF1R), belonging to the large class of tyrosine kinase receptors, is a transmembrane receptor that is activated by insulin-like growth factor 1 (IGF-1). The IGF1R may originate from a mammal including primates such as humans and monkeys, and rodents such as mice and rats. For example, the IGF1R may be a polypeptide including the amino acid sequence encoded by the nucleotide sequence (mRNA) of GenBank Accession No. NM_000875.3.

Ephrin receptors are cell surface receptor tyrosine kinases, and mediate the ephrin signaling implicated in the regulation of embryonic development processes including axon guidance, formation of tissue boundaries, cell migration, and segmentation. Ephrin receptors may originate from a mammal including primates such as humans and monkeys, and rodents such as mice and rats. For example, ephrin receptors may be polypeptides including the amino acid sequence encoded by the nucleotide sequences (mRNAs) of GenBank Accession Nos. NM_004440.3, NM_004438.3, NM_004431.3, NM_004442.6, NM_017449.3, NM_004093.3, NM_004441.4, NM_182472.2, NM_005232.4, NM_005233.5, NM_173641.2, NM_001099439.1, NM_001080448.2, NM_01080448.2, NM_004443.3, NM_182689.1, NM_004428.2, NM_004439.5, NM_001962.2, NM_004429.4, NM_182644.2, NM_004952.4, NM_173655.2, NM_182690.2, NM_020526.3, NM_001406.3, NM_005227.2, and NM_182685.1.

The fibroblast growth factor receptors (FGFRs) are receptors that bind to members of the fibroblast growth factor family of proteins. Some of these receptors are involved in pathological conditions. For example, a point mutation in FGFR3 can lead to achondroplasia. Five distinct FGFRs have been identified in vertebrates and all of them belong to the tyrosine kinase superfamily (FGFR1 to FGFR4 & FGFR6). FGFR1 may include the amino acid sequence encoded by the nucleotide sequence (mRNA) of GenBank Accession Nos. NM_001174063 or NM_001079908, FGFR2 may include the amino acid sequence encoded by the nucleotide sequence (mRNA) of GenBank Accession Nos. NM_000141 or NM_010207, FGFR3 may include the amino acid sequence encoded by the nucleotide sequence (mRNA) of GenBank Accession Nos. NM_000142 or NM_001163215, and FGFR4 may include the amino acid sequence encoded by the nucleotide sequence (mRNA) of GenBank Accession Nos. NM_002011 or NM_008011.

The transferrin receptor is a carrier protein for transferrin. It imports iron into the cells by internalizing the transferrin-iron complex through receptor-mediated endocytosis (internalization) and is regulated in response to intracellular iron concentration. The transferrin receptor may originate from a mammal including primates such as humans and monkeys, and rodents such as mice and rats. For example, the transferrin receptor may be a polypeptide including the amino acid sequence encoded by the nucleotide sequence (mRNA) of GenBank Accession Nos. NM_001128148.1, NM_003234.2, NM_001206855.1, NM_003227.3, BC001188.1, or M11507.1.

The low-density lipoprotein (LDL) receptor is a cell surface receptor that recognizes the apoprotein B100 which is embedded in the phospholipid outer layer of LDL particles. It mediates the endocycosis of cholesterol-rich LDL. The LDL receptor may originate from mammals and rodents. For example, the LDL receptor may be a polypeptide including the amino acid sequence encoded by the nucleotide sequence (mRNA) of GenBank Accession No. NM_000527.4, NM_001195802.1, NM_001195799.1, NM_001195803.1, NM_001195800.1, or NM_001195798.1.

Cluster of differentiation (clusters of designation; CD) molecules can act as receptors or ligands implicated in various cellular processes including cell signaling and cell adhesion, and are numbered up to 350 most recently for humans. The CD molecule may originate from a mammal including primates such as humans and monkeys, and rodents such as mice and rats. For example, the CD molecules may be from any source, particularly, may be CD44, CD47 or a variant thereof. In embodiments, the CD molecules may be polypeptides including the amino acid sequence encoded by the nucleotide sequences (mRNAs) of GenBank Accession Nos. (NM_000610.3, NM_001728.3, X55150.1), respectively.

G-protein-coupled receptors (GPCRs) are transmembrane receptors that activate signal transduction pathways and cellular responses and are involved in many diseases. GPCRs can be grouped into 6 classes based on sequence homology and functional similarity: class A or class 1 (rhodopsin-like receptors); class B or class 2 (secretin receptor family); class C or 3 (metabotropic glutamate/pheromone); class D or class 4 (fungal mating pheromone receptors); class E or class 5 (cyclic AMP receptors); and class F or class 6 (frizzled/smoothened). The GPCRs may originate from a mammal including primates such as humans and monkeys, and rodents such as mice and rats. For example, the GPCRs may be cancer metastasis-related chemokine receptors (rhodopsin-like receptor subfamily), e.g., CXC chemokine receptor, CC chemokine receptor, CX3C chemokine receptor, etc. In one embodiment, the GPCRs may be polypeptides including the amino acid sequence encoded by nucleotide sequences (mRNAs) of GenBank Accession Nos. NM_001123041.2, NM_005508.4 NM_005201.3, and NM_016602.2, respectively.

The tetraspanins (e.g., CD9, CD81, CD151, CD63, CD37, CD53, NET1, NET2, NET4, NET5, NET6, TM4SF6, Tspan2, Tspan3, TM4B, etc.) are a family of transmembrane proteins with 33 mammalian members, which are variably found on the plasma membrane and within various intracellular organelles and granules in nearly all cell and tissue types. In contrast to many other cell surface proteins, tetraspanins do not have an obvious receptor function. Tetraspanins are found in the endosomal system and in lysome-related organelles. These include the dense granules and alpha-granules in platelets, melanosomes in melanocytes, cytotoxic granules in T-cells, Weibel-Palade bodies in endothelial cells and Major Histocompatibility Complex II (MHCII) compartments in dendritic cells. Furthermore, in many cell types, late endosomes/MVBs (multivesicular bodies) can be triggered to fuse with the cell surface and release exosomes that are functionally related to cancer progression and metastasis. These suggest that tetraspanins could be used as the driver or the target for membrane depletion. CD9 may include the amino acid sequence encoded by the nucleotide sequence (mRNA) of GenBank Accession Nos. NM_001769 or NM_007657, CD81 may include the amino acid sequence encoded by the nucleotide sequence (mRNA) of GenBank Accession Nos. NM_004356 or NM_133655, CD 151 may include the amino acid sequence encoded by the nucleotide sequence (mRNA) of GenBank Accession Nos. NM_001039490 or NM_001111049, CD63 may include the amino acid sequence encoded by the nucleotide sequence (mRNA) of GenBank Accession Nos. NM_001040034 or NM_001042580, CD37 may include the amino acid sequence encoded by the nucleotide sequence (mRNA) of GenBank Accession Nos. NM_001040031 or NM_007645, CD53 may include the amino acid sequence encoded by the nucleotide sequence (mRNA) of GenBank Accession Nos. NM_000560 or NM_007651, NET1 may include the amino acid sequence encoded by the nucleotide sequence (mRNA) of GenBank Accession Nos. NM_001047160 or NM_001047159, NET2 may include the amino acid sequence encoded by the nucleotide sequence (mRNA) of GenBank Accession Nos. NM_012338 or NM_173007, NET6 may include the amino acid sequence encoded by the nucleotide sequence (mRNA) of GenBank Accession Nos. NM_014399 or NM_025359, TM4SF6 may include the amino acid sequence encoded by the nucleotide sequence (mRNA) of GenBank Accession Nos. NM_001278743, NM_001278742, NM_001278741, NM_001278740, NM_003270, or NM_019656, Tspan2 may include the amino acid sequence encoded by the nucleotide sequence (mRNA) of GenBank Accession Nos. NM_005725, NM_001243132, or NM_027533, Tspan3 may include the amino acid sequence encoded by the nucleotide sequence (mRNA) of GenBank Accession Nos. NM_001168412, NM_198902, NM_005724, or NM_019793, and TM4B (TSPAN16) may include the amino acid sequence encoded by the nucleotide sequence (mRNA) of GenBank Accession Nos. NM_001282510, NM_001282509, or NM_012466.

The composition for target membrane protein depletion does not simply inhibit the activity of a target membrane protein that mediates cell signals relevant to abnormal cell states, or is involved in the etiology of diseases including cancer, by binding, but acts to deplete the target membrane protein by triggering endocytosis (internalization) and degradation.

In order for the composition for target membrane protein depletion to effectively work, both the driver membrane protein and the target membrane protein must be present on the same cell (e.g., the same cell membrane). There is no particular limitation in distance between the driver membrane protein and target membrane protein on the same cell membrane in consideration of the flexibility and fluidity of the plasma membrane and the levels of the target membrane protein in the plasma membrane (e.g., expression levels in abnormal cells).

The first binding domain and the second binding domain of the dual binding molecule contained in the composition for target membrane protein depletion may each be independently selected from the group consisting of antibodies to the driver membrane protein or the target membrane protein, antibody fragments (e.g., antigen binding fragments) thereof, and antibody mimics (also known as antibody mimetics). Specific examples of the first and second binding domains include, for instance, antibodies (e.g., full immunoglobulin form), scFv antibodies, phage antibodies, domain antibodies, DARPins (Designed Ankyrin Repeat Proteins), fibronectin domains, kringle domains, nanobodies, peptibodies, peptides, or aptides, or a combination thereof.

For example, the first binding domain may be derived from an antibody against the driver membrane protein or from an antigen-binding fragment thereof while the second binding domain may be derived from an antibody against the target membrane protein or from an antigen-binding fragment thereof. Thus, the dual binding molecule may be a bispecific (dual binding) antibody for both the driver membrane protein and the target membrane protein, including respective binding domains to the deriver membrane protein and the target membrane protein.

In one embodiment, the bispecific antibody may include:
an antibody against the driver membrane protein or an antigen binding fragment thereof; and
an antibody against the target membrane protein or an antigen binding fragment thereof,
wherein the antibody against the target membrane protein or the antigen binding fragment thereof is linked to the C- or N-terminus of the antibody against the driver membrane protein or the antigen binding fragment thereof.

In this regard, the bispecific antibody may possess vertical asymmetry, wherein N-terminal part (e.g., N-terminal part from Fc region) and C-terminal part (e.g., C-terminal part from Fc region) of the bispecific antibody are structurally different (e.g., they are different from each other and independently selected from the group consisting of a scFv fragment, (scFv)$_2$, a Fab fragment, a Fab' fragment, a F(ab')$_2$ fragment, and antibody mimics such as DARPins) and/or functionally different (e.g., N-terminus and C-terminus specifically recognize and/or bind to different proteins) from each other. Alternatively, the bispecific antibody having vertical asymmetry may comprise an antibody in a complete form (e.g., an IgG form) and an antibody fragment (e.g., a scFv fragment, (scFv)$_2$, a Fab fragment, a Fab' fragment, a F(ab')$_2$ fragment, or an antibody mimics such as DARPin) linked to the C-terminus or N-terminus of the antibody, wherein the antibody and the antibody fragment may recognize the same with or different antigen from each other.

In another embodiment, the bispecific antibody may include:
a single-chain antibody (scFvFc) to the driver membrane protein or an antigen-bind ing fragment thereof (scFv); and
a single-chain antibody (scFvFc) to the target membrane protein or an antigen-bind ing fragment thereof (scFv),
wherein the single-chain antibody against the driver membrane protein or the antigen-binding fragment thereof is conjugated with the single-chain antibody to the driver membrane protein or the antigen-binding fragment thereof, to form bilateral asymmetry.

Therefore, the bispecific antibody may be of bilateral asymmetry, wherein the two single-chain antibodies specifically bind to different proteins from each other.

In a composition for target membrane protein depletion or in the bispecific antibody, it is important for the antibody against the driver membrane protein to act to mediate both internalization into a cell and degradation. To perform its functions, the antibody against the driver membrane protein may have a whole antibody form (e.g., a full immunoglobulin from). On the other hand, because it is important for the antibody against the target membrane protein to specifically recognize and bind to the target membrane protein, the antibody may be in the form of an antigen-binding fragment or a whole antibody. In one embodiment, therefore, the bispecific antibody may include a whole antibody against the driver membrane protein, and an antigen binding fragment of an antibody against the target membrane protein, wherein the antigen binding fragment is linked to the C-terminus of the whole antibody against the driver membrane.

To account for the distance between the driver membrane protein and the target membrane protein, the first binding domain for the driver membrane protein may be separated at a sufficient distance from the second binding domain for the target membrane protein in the dual binding molecule to facilitate binding both the target membrane protein and the driver membrane protein. Thus, the dual binding molecule may have a structure in which the first binding domain may be joined to the second binding domain via a flexible linker.

In the bispecific antibody, the antibody against the driver membrane protein or an antigen-binding fragment thereof may be linked to the antibody against the target membrane protein or an antigen-binding fragment thereof, directly or through a peptide linker. The peptide linker may be composed of 1 to 100 amino acids, 2 to 50 amino acids, or 5 to 20 amino acids. No limitations are imposed to the kind of the amino acids used in the peptide linker. For example, the peptide linker may include at least one residue selected from among Gly, Asn, and Ser, or may include neutral amino acids such as Thr and/or Ala. An amino acid sequence suitable for use in the peptide linker may be known in the art. Also, the peptide linker be of any length provided it does not negate the function of the bispecific antibody.

In one embodiment, the antibody against the target membrane protein or an antigen-binding fragment thereof may be selected from the group consisting of an anti-EGFR antibody, an anti-HER2 antibody, an anti-HER3 antibody, an anti-VEGFR antibody, an anti-PDGFR antibody, an anti-IGF-1R antibody, and antigen-binding fragments thereof. The anti-EGFR antibody may be selected from the group consisting of cetuximab (ERBITUX® (cetuximab)), panitumumab, matuzumab, necitumumab, nimotuzumab, zalutumumab, MM-151 (an oligoclonal therapeutic consisting of a mixture of three fully human monoclonal antibodies designed to bind to non-overlapping epitopes of EGFR), an antibody composed of a heavy variable region including an amino acid sequence as set forth in SEQ ID NO: 109 or 113 and a light variable region including an amino acid sequence as set forth in SEQ ID NO: 110 or 114. The anti-HER2 antibody may be selected from among trastuzumab (Herceptin) or pertuzumab. The anti-HER3 antibody may be RG-7597 (humanized IgG1 monoclonal antibody). For example, the anti-VEGFR2 (KDR) antibody, and the anti-PDGFR antibody may be ramucirumab and olaratumab (IMC-3G3), respectively. Cixutumumab (IMC-A12) may be suitably used as an anti-IGF-1R antibody.

As mentioned above, an antibody against the target membrane protein may exist as a whole antibody or an antigen-binding fragment in the bispecific antibody.

The antibody against the driver membrane protein or an antigen-binding fragment thereof may be an anti-c-Met antibody, or an antibody capable of effectively internalizing a membrane protein, or an antigen-binding fragment thereof. The antibody against the driver membrane protein may be in the form of a whole antibody or an antigen-binding fragment.

As used herein, the term "antigen-binding fragment" refers to a fragment of an intact immunoglobulin that binds to antigens. For example, the antigen-binding fragment may be a scFv fragment, (scFv)$_2$, a Fab fragment, a Fab' fragment or a F(ab')$_2$ fragment, but is not limited thereto.

A Fab fragment is composed of one variable and one constant domain from the light chain, and one variable and one constant ($C_{H1}$) domain from the heavy chain, retaining one antigen-binding site.

A Fab' fragment is different from Fab in that the Fab' further includes a hinge region including at least one cysteine residue at the C-terminus of the heavy chain $C_{H1}$ domain. A F(ab')$_2$ fragments forms as two Fab' fragments are joined by a disulfide bond between the cysteine residues of the hinge region.

A Fv fragment is a minimal antibody fragment composed only of variable domains from the heavy chain and the light chain. Recombinant techniques for producing the Fv are well known in the art. In a two-chain Fv fragment, the heavy chain variable domains are associated with the light chain variable domains via a non-covalent bond. A single-chain Fv fragment has a structure in which a heavy chain variable domain and a light chain variable domain are covalently joined to each other at the C-terminus directly or via a peptide linker, and two single-chain Fv fragments can form a dimer as in a two-chain Fv fragment. The peptide linker may be composed of 1 to 100 amino acid residues, 2 to 50 amino acid residues, or 5 to 20 amino acid residues, with no limitations imposed on the kind of the amino acid residues. For example, the peptide linker may include at least one residue selected from among Gly, Asn and Ser, and may also include neutral amino acids such as Thr and/or Ala. Amino acid sequences suitable for use in the peptide linker may be those well known in the art. So long as it has no negative influence on the function of the antigen-binding fragment, the length of the peptide linker may be appropriately adjusted.

An antigen binding fragment can be prepared using a protease (for example, a whole antibody is cleaved into two Fab fragments by digestion with papain while pepsin is used to produce an F(ab')$_2$ fragment). Alternatively, a genetic recombinant technique may be useful for producing an antigen binding fragment.

In one embodiment, the bispecific antibody may include an anti-c-Met antibody, and an scFv, an (scFv)$_2$, an Fab, an Fab' or an F(ab')$_2$ fragment of an antibody against the target membrane protein (e.g., an anti-EGFR antibody, an anti-HER2 antibody, an anti-HER3 antibody, an anti-VEGFR antibody, or an anti-PDGFR antibody), wherein the fragment is linked to the C-terminus of the anti-c-Met antibody, with preference for the scFv. For example, the scFv, (scFv)$_2$, Fab, Fab' or F(ab')$_2$ fragment of the anti-EGFR antibody includes a heavy chain variable domain including the amino acid sequence as set forth in SEQ ID NO: 109 or 113 and a light chain variable domain including the amino acid sequence as set forth in SEQ ID NO: 110 or 114. In one embodiment, thus, the bispecific antibody includes an anti-c-Met antibody, and an scFv, (scFv)$_2$, Fab, Fab' or F(ab')$_2$ fragment of anti-EGFR antibody, wherein the fragment is linked to the C-terminus of the anti-c-Met antibody and includes a light chain variable domain including the amino acid sequence as set forth in SEQ ID NO: 109 or 113, and a heavy chain variable domain including the amino acid sequence as set forth in SEQ ID No: 110 or 114.

The anti c-Met antibody may be any antibody or antigen-binding fragment that acts on c-Met to induce c-Met intracellular internalization into a cell and degradation. The anti c-Met antibody or antigen-binding fragment thereof may recognize a specific region of c-Met, e.g., a specific region in the SEMA domain, as an epitope.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may include the amino acid sequence of SEQ ID NO: 79, and is an extracellular domain that functions to bind HGF. A specific region of the SEMA domain, that is, a region including the amino acid sequence of SEQ ID NO: 71, which corresponds to a range from amino acid residues 106 to 124 of the amino acid sequence of the SEMA domain (SEQ ID NO: 79), is a loop region between the second and the third propellers within the epitopes of the SEMA domain. This region acts as an epitope for the anti c-Met antibody provided.

The term "epitope," as used herein, refers to an antigenic determinant, a part of an antigen recognized by an antibody. In one embodiment, the epitope may be a region including 5 or more contiguous (consecutive or non-consecutive) amino acid residues within the SEMA domain (SEQ ID NO: 79) of c-Met protein, for instance, 5 to 19 consecutive amino acid residues of SEQ ID NO: 71. For example, the epitope may be a polypeptide including 5 to 19 contiguous amino acids selected from among partial combinations of the amino acid sequence of SEQ ID NO: 71, wherein the polypeptide includes the amino sequence of SEQ ID NO: 73 (EEPSQ) serving as an essential element for the epitope. The amino sequence of SEQ ID NO: 73 ranges from position 143 to position 147 of SEMA domain (SEQ ID NO: 79) of c-Met protein. For example, the epitope may be a polypeptide including, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Thus, the anti c-Met antibody may specifically bind to an epitope which has 5 to 19 consecutive or non-consecutive amino acids selected from among partial combinations of the amino acid sequence of SEQ ID NO: 71, including SEQ ID NO: 73 as an essential element. For example, the anti c-Met antibody may specifically bind to an epitope including the amino acid sequence of SEQ ID NO: 71, SEQ ID NO: 72, or SEQ ID NO: 73.

In one embodiment, the anti c-Met antibody or an antigen-binding fragment thereof may include:

at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, SEQ ID NO: 2, or an amino acid sequence comprising 8-19 consecutive amino acids of SEQ ID NO: 2 including the $3^{rd}$ to $10^{th}$ positions of SEQ ID NO: 2; and (c) a CDR-H3 comprising the amino acid sequence of SEQ ID NO: 6, SEQ ID NO: 85, or an amino acid sequence comprising 6-13 consecutive amino acids within SEQ ID NO: 85 including the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, SEQ ID NO: 86, or an amino acid sequence comprising 9-17 consecutive amino acids of SEQ ID NO: 89 including the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
$Xaa_1$-$Xaa_2$-Tyr-Tyr-Met-Ser, wherein $Xaa_1$ is absent or Pro or Ser, and $Xaa_2$ is Glu or Asp, Formula II
(SEQ ID NO: 5)
Arg-Asn-$Xaa_3$-$Xaa_4$-Asn-Gly-$Xaa_5$-Thr, wherein $Xaa_3$ is Asn or Lys, $Xaa_4$ is Ala or Val, and $Xaa_5$ is Asn or Thr, Formula III
(SEQ ID NO: 6)
Asp-Asn-Trp-Leu-$Xaa_6$-Tyr, wherein $Xaa_6$ is Ser or Thr, Formula IV
(SEQ ID NO: 7)
Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala wherein $Xaa_7$ is His, Arg, Gln, or Lys, $Xaa_8$ is Ser or Trp, $Xaa_9$ is His or Gln, and $Xaa_{10}$ is Lys or Asn, Formula V
(SEQ ID NO: 8)
Trp-$Xaa_{11}$-Ser-$Xaa_{12}$-Arg-Val-$Xaa_{13}$ wherein $Xaa_{11}$ is Ala or Gly, $Xaa_{12}$ is Thr or Lys, and $Xaa_{13}$ is Ser or Pro, and Formula VI
(SEQ ID NO: 9)
$Xaa_{14}$-Gln-Ser-Tyr-Ser-$Xaa_{15}$-Pro-$Xaa_{16}$-Thr wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may include a heavy variable region including a polypeptide (CDR-H1) comprising an amino acid sequence selected from the group consisting of SEQ ID NOS: 1, 22, 23, and 24, a polypeptide (CDR-H2) comprising an amino acid sequence selected from the group consisting of SEQ ID NOS: 2, 25, and 26, and a polypeptide (CDR-H3) comprising an amino acid sequence selected from the group consisting of SEQ ID NOS: 3, 27, 28, and 85; and a light variable region including a polypeptide (CDR-L1) comprising an amino acid sequence selected from the group consisting of SEQ ID NOS: 10, 29, 30, 31, 32, 33 and 106, a polypeptide (CDR-L2) comprising an amino acid sequence selected from the group consisting of SEQ ID NOS: 11, 34, 35, and 36, and a polypeptide (CDR-L3) comprising an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering.

Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

In one embodiment of the anti c-Met antibody or antigen-binding fragment, the variable domain of the heavy chain comprises the amino acid sequence of SEQ ID NO: 17, 74, 87, 90, 91, 92, 93, or 94 and the variable domain of the light chain comprises the amino acid sequence of SEQ ID NO: 18, 19, 20, 21, 75, 88, 95, 96, 97, 98, 99, or 107.

In one embodiment, the anti c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include all the antibodies defined in Korean Patent Publication No. 2011-0047698.

In the anti-c-Met antibody, the remaining portion of the light chain and the heavy chain portion excluding the CDRs, the light chain variable region, and the heavy chain variable region as defined above, that is the light chain constant region and the heavy chain constant region, may be those from any subtype of immunoglobulin (e.g., IgA, IgD, IgE, IgG (IgG1, IgG2, IgG3, IgG4), IgM, and the like).

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the 21$^{st}$ to 240$^{th}$ positions of SEQ ID NO: 70;

an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 70 or the amino acid sequence from the 21$^{st}$ to 240$^{th}$ positions of SEQ ID NO: 70;

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 108.

According to an embodiment, the anti-c-Met antibody may include a heavy chain including the amino acid sequence from the 18$^{th}$ to 460$^{th}$ positions of SEQ ID NO: 66 and a light chain including the sequence from the 21$^{st}$ to 240$^{th}$ positions of SEQ ID NO: 68, or a heavy chain including the amino acid sequence from the 18$^{th}$ to 460$^{th}$ positions of SEQ ID NO: 66 and a light chain including the sequence of SEQ ID NO: 108.

The polypeptide of SEQ ID NO: 70 is a light chain including human kappa (K) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, and Akt phosphorylation inhibition.

In another embodiment, the anti c-Met antibody may include a light chain complementarity determining region including the amino acid sequence of SEQ ID NO: 106, a light chain variable region including the amino acid sequence of SEQ ID NO: 107, or a light chain including the amino acid sequence of SEQ ID NO: 108.

Another embodiment provides a method of target membrane protein depletion, including treating a cell with the composition for target membrane protein depletion or with the dual binding molecule (or the bispecific antibody) contained in the composition or administering the composition for target membrane protein depletion or with the dual binding molecule (or the bispecific antibody) contained in the composition to a subject in need of the target membrane protein depletion. The method of target membrane protein depletion may further include the step of identifying the subject in need of the target membrane protein depletion, prior to the step of administering.

In accordance with a further aspect, a use of the composition or the dual binding molecule (or bispecific antibody) in target membrane protein depletion is provided.

The cell may be any viable cell that originates from a mammal including primates such as humans and monkeys, or rodents such as mice and rats. In one embodiment, the cell may be a cancer cell and expresses a driver membrane protein, for example, a c-Met protein in the plasma membrane. The cell may exist in the body or may be an isolated cell from the body. The subject may be a mammal including primates such as humans and monkeys, or rodents such as mice and rats, and may be an individual with a disease associated with the target membrane protein, for example a cancer.

c-Met is known to be co-expressed with RTKs including EGFR in cancer cells, and a crosstalk exists between c-Met and other RTKs, accounting for the tolerance of the cancer cells to anticancer agents. Accordingly, suppression of both c-Met and RTKs such as EGFR or HER2 envisages the development of a novel anticancer agent that overcomes tolerance to and problems with conventional anticancer agents.

Another embodiment provides a pharmaceutical composition for prevention and/or treatment of a cancer, including the composition for target membrane protein depletion or the dual binding molecule (or the bispecific antibody) as an active ingredient and a carrier, diluent, or excipient.

Another embodiment provides a method of preventing and/or treating cancer, by administering the composition for target membrane protein depletion or the dual binding molecule (e.g., the bispecific antibody) used in the composition in a pharmaceutically effective amount to a subject in need of preventing and/or treating cancer. The method of preventing and/or treating cancer may include a step of identifying the subject in need of preventing and/or treating cancer, prior to the step of administering.

Another embodiment provides a use of the composition for target membrane protein depletion or the dual binding molecule (or the bispecific antibody) in the prevention and/or treatment of a cancer.

The method can be used to treat or prevent any type of cancer. Target membrane proteins may be selected based on the type of cancer to be treated. Examples of cancer include, but are not limited to, squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, or head or neck cancers. The cancer may be a primary cancer or a metastatic cancer. Particularly, the cancer may be cancer tolerant to a conventional anticancer agent, for example, cancer tolerant to an antagonist of the target membrane protein.

The pharmaceutical composition may include a pharmaceutically acceptable carrier, diluent and/or excipient in addition to the composition for target membrane protein depletion or the dual binding molecule (or the bispecific antibody) used in the composition.

So long as it is usually used in drug formulations of antibodies, any pharmaceutically acceptable carrier may be contained in the pharmaceutical composition. Examples of the pharmaceutically acceptable carrier available for the pharmaceutical composition may include lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methyl hydroxy benzoate, propyl hydroxy benzoate, talc, magnesium stearate, mineral oil, or any combination thereof, but are not limited thereto. In addition to these components, the pharmaceutical composition may further include a typical additive selected from the group consisting of a diluent, an excipient, a lubricant, a humectant, a sweetener, a flavor enhancer, an emulsifier, a suspending agent, a preservative, and a combination thereof.

The pharmaceutical composition may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition may be coated or formulated to protect the active ingredient from being degraded in the stomach because proteins or peptides are digested by pepsin. In addition, the administration may be performed with the aid of an instrument adapted for delivering the pharmaceutical composition to target cells.

The effective amount may vary depending on various factors including the type of formulation, the patient's age, weight, and sex, the severity of the disorder being treated, diet, the time of administration, the route of administration, the rate of excretion, and sensitivity. For example, the composition may be administered at a single dose of from 0.001 mg to 100 mg/kg for adults. The term "pharmaceutically effective amount," as used herein, refers to an amount used in effectively preventing or treating cancer.

According to a method that is well known to those skilled in the art, the pharmaceutical composition may be formulated, together with pharmaceutically acceptable carriers and/or excipients, into unit dose forms, or may be included within a multiple dose package. In this context, the pharmaceutical composition may be formulated into solutions in oil or aqueous media, suspensions, syrup, emulsions, elixirs, powders, granules, tablets, or capsules, and may further include a dispersant or a stabilizer.

The pharmaceutical composition may be administered alone or in combination with other therapeutics. In this case, they are administered sequentially or simultaneously together with conventional therapeutics.

The pharmaceutical composition including the dual binding molecule (e.g., bispecific antibody) can be formulated into immunoliposomes. Liposomes including an antibody can be prepared using methods that are well-known in the art. The immunoliposomes may be produced from a lipid composition including phosphatidylcholine, cholesterol, and PEGylated phosphatidylethanolamine by reverse-phase evaporation. For example, Fab' can be conjugated to liposomes by disulfide reformation. The liposome may further contain an anticancer agent such as doxorubicin.

The subject to be administered with the pharmaceutical composition or in need of preventing and/or treating cancer may include a mammal including primates such as humans or monkeys, and rodents such as rats and mice, or cells or tissues derived (separated) therefrom, but are not limited thereto, and may be, for example, a cancer patient resistant to an antagonist of the target membrane protein As elucidated above, co-existence of a target membrane protein and a driver protein which is responsible for the internalization into a cell and degradation of the target membrane protein in the same plasma membrane is prerequisite for target membrane protein depletion. Under this condition, the dual binding molecule (trigger) conjugates the driver with the target protein, and thereby triggers the internalization into a cell and degradation of the driver together with the target. The driver and target proteins must coexist in the same plasma membrane, and can undergo internalization into a cell and intracellular degradation. The dual binding molecule (trigger) is a molecule capable of binding to both a target membrane protein and a driver with high affinity, and triggers the internalization into a cell and degradation of the driver, thereby drawing the target into the cytoplasm and resulting in the degradation of the target.

Figure 3:
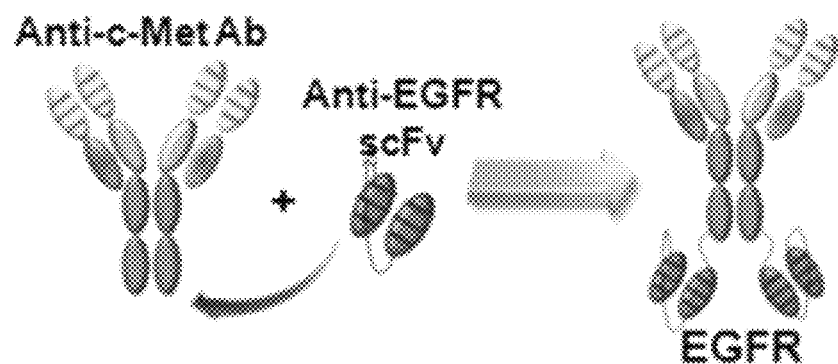
FIG. 3 is a schematic diagram illustrating components (bispecific antibody: BsAb) used in a system for membrane protein depletion.

FIG. 3 is a schematic diagram illustrating a driver protein and a trigger (dual binding antibody) according to one embodiment. EGFR, a membrane protein known as an anticancer target, is inhibited when treated with an antibody thereto, but is not depleted from the plasma membrane of viable cells. In one embodiment, the driver is a c-Met protein containing an epitope, and the dual binding antibody is a bispecific antibody exhibiting high affinity for both the epitope and the driver, and allows the effective internalization into a cell and degradation of c-Met without provoking an adverse effect (agonism).

After being applied to clinical samples in practice, the technology of target membrane protein depletion is expected to draw the following effects:

1. Provision of a novel epochal tool and method for research into functions of membrane proteins in the cell biology field, which can be commercialized similar to siRNA technology.

2. Expansion of a bispecific antibody pipeline: bispecific antibodies against both c-Met and a secondary target, where the secondary target is expected to have a synergistic efficacy when co-inhibited with c-Met, are produced and can be used as anticancer agents due to their ability to deplete the anticancer targets, thus expanding the anticancer agent pipeline.

3. Increased efficacy for anticancer therapy-related major targets such as EGFR, HER2, etc.: the technique allows for degradation of all of the homodimers and heterodimers of the targets, thus suppressing the oncogenetic functions of the targets.

4. c-Met-related tolerance is overcome and an antibody agent with enhanced c-Met-related anticancer activity is produced.

A better understanding of the present invention may be obtained through the following examples which are set forth to illustrate, but are not to be construed as limiting the present invention.

EXAMPLES

Reference Example 1

Construction of Anti-1-Met Antibody 1.1. Production of "AbF46", a Mouse Antibody to c-Met 1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 9, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™ 3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invitrogen) (tube A), and in another 15 ml tube, 100 ul (microliter) of Freestyle™ MAX reagent and 2 ml of OptiPro™ SFM were mixed (tube B), followed by mixing tube A and tube B and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invitrogen) (tube A), and in another 15 ml tube, 100 ul (microliter) of Freestyle™ MAX reagent and 2 ml of OptiPro™ SFM were mixed (tube B), followed by mixing tube A and tube B and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved in the following steps. First, six complementary determining regions (CDRs) were defined according to Kabat numbering. The CDRs are given in Table 1, below.

TABLE 1

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |

TABLE 1-continued

| CDR | Amino Acid Sequence |
|---|---|
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After affinity maturation of the constructed libraries for c-Met, the nucleotide sequence of scFv from each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 2

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an Opti-CHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invitrogen) (tube A), and in another 15 ml tube, 100 ul (microliter) of Freestyle™ MAX reagent and 2 ml of OptiPro™ SFM were mixed (tube B), followed by mixing tube A and tube B and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invitrogen) (tube A), and in another 15 ml tube, 100 ul (microliter) of Freestyle™ MAX reagent and 2 ml of OptiPro™ SFM were mixed (tube B), followed by mixing tube A and tube B and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as L3-1Y-IgG2 (uAbF46-H4-A1 (IgG2 Fc)).

1.9: Analysis for Epitope of huAbF46

(1) Epitope Mapping

1) Preparation of Peptide for Epitope Mapping of huAbF46

543 amino acid sequences including the SEMA domain of c-Met and structures thereof are represented in PDB (Protein Database) ID: 1UZY, and 6,063 other sequences capable of producing a conformational epitope and a discontinuous epitope were designed and synthesized based on the 543 amino acid sequences by using a Chemically Linked Peptides on Scaffolds (CLIPS) technology (Timmerman et al., 2007 Functional reconstruction and synthetic mimicry of a conformational epitope using CLIPS™ technology. J. Mol. Recognit. 20: 283-00). The peptide array fabrication will now be described in more detail. The CLIPS technology developed by PepScan is used to prepare peptides having an intrinsic structure called CLIPS rather than linear peptides having a length of about 15 amino acids, prepared using a known typical method. The binding affinity of huAbF46 with the linear peptides and the CLIPS peptides was measured. Among the CLIPS peptides, T2 CLIPS peptides are prepared such that two cysteines are linked together to form a loop so that the peptides have an artificial structure, and T3 CLIPS peptides are prepared such that three cysteines are linked together to form a loop so that the peptides have an artificial structure. In addition, binding-type peptides such as T2T3 or T2T2 CLIPS peptides may be prepared.

A total number of 6,063 peptides were prepared for epitope mapping (peptide array design was applied to PepScan). In this regard, $1^{st}$ through $529^{th}$ peptides, which are typical linear peptides, were prepared such that the peptides had a length of 15 amino acids and an overlapped region between certain regions. 530th through 1,058th peptides were prepared by introducing 1st through 529th peptides to T2 CLIPS peptides. 1,059th through 2,014th peptides, i.e., a total number of 956 peptides, were prepared by linking two peptides each having 15 amino acids to T3 CLIPS peptides. 2,015th through 6,063rd, i.e., a total number of 4,048 peptides, were prepared as peptides for searching epitopes having conformational and discontinuous structures through binding between peptide groups having 8 to 35 amino acid residues.

For example, a peptide array including T2 CLIPS peptides was prepared as follows. 0.5 mM of a 1,3-bis(bromomethyl) benzene solution including T2 CLIPS peptides was dissolved in ammonium bicarbonate (20 mM, pH 7.9)/acetonitrile (1:1 (v/v), and the resultant solution was added to a peptide array. The T2 CLIPS peptides as a template were bound to two cysteine side chains existing in a solid-phase bound peptide of the peptide array (455-well plate having 3 ul of wells). The peptide array was slowly shaken in the solution for 30 to 60 minutes. Lastly, the peptide array was sufficiently washed with a large amount of water, was ultrasonically fragmented in a lysate-buffer containing 1% SDS/0.1% beta-mercaptoethanol in PBS (pH 7.2) at 70° C. for 30 minutes, and further ultrasonically fragmented in water for 45 minutes. T3 CLIPS peptides were prepared using the same method as described above, except that the T3 CLIPS peptides as a template were bound to three cysteine side chains.

As a result of performing epitope mapping by using the peptides by ELISA, a core epitope of huAbF46 was confirmed to be EEPSQ (SEQ ID NO: 73) peptides consisting of 168th through 171st amino acids of c-Met protein.

2) ELISA for Epitope Mapping of huAbF46

For epitope mapping, PEPSCAN-based ELISA was performed using a total number of 529 linear and CLIPS peptides. The peptides were maintained at room temperature for 30 minutes by using a 5% blocking solution to provoke a reaction (4% ovalbumin, 5% horse serum, and 1% Tween 80). Then, 1 to 100 ug/ml of huAbF46 antibodies maintained in PBS containing 1% Tween 80 at 4° C. overnight were reacted with the peptides and the resultant product was then washed. Thereafter, the resultant product was treated with rabbit-anti-sheep antibody (SIGMA) and washed with PBS, and the washed product was then treated with peroxidase-attached swine-anti-rabbit antibody (SIGMA) and washed with PBS. Then, the resultant was treated with 2 ul/ml of peroxidase 2,2'-azino-di-3-ethylbenzthiazoline sulfonate (ABTS) (SIGMA) in 3% $H_2O_2$, and a color reaction was measured after 1 hour.

As a result, as illustrated in FIG. 15, only the peptides including EEPSQ (SEQ ID NO: 3) of both the linear peptides and the CLIPS peptides exhibited a specific ELISA positive reaction, and thus the huAbF46 antibody was confirmed to recognize the linear and conformational epitopes of c-Met.

In addition, an ELISA was performed in the same manner as described above by using polypeptides with E168D mutation, which is a representative SEMA domain mutation of c-Met known to be found in some patients with lung cancer or ovarian cancer, among the epitopes including the peptides including EEPSQ (SEQ ID NO:73). The results are shown in Table 3 below.

TABLE 3

| Core peptide sequence | Synthesized peptide sequence | ELISA value (antibody binding of huAbF46) |
|---|---|---|
| EEPSQ (SEQ ID NO: 73) | FAPQIEEPSQCPDCVVSALGAKVL (SEQ ID NO: 119) | 2063 |
| | CSPQIEEPSQC (SEQ ID NO: 120) | 1306 |
| | CPQIEEPSQAC (SEQ ID NO: 121) | 2157 |
| | CQIEEPSQAPC (SEQ ID NO: 122) | 2744 |
| | CIEEPSQAPDC (SEQ ID NO: 123) | 2239 |
| | CEEPSQAPDAC (SEQ ID NO: 124) | 2829 |
| EDPSQ (SEQ ID NO:125) | FSPQIEDPSQCPDCWSALGAKVL (SEQ ID NO: 126) | 172 |
| | CSPQIEDPSQC (SEQ ID NO: 127) | 121 |
| | CPQIEDPSQAC (SEQ ID NO: 128) | 138 |
| | CQIEDPSQAPC (SEQ ID NO: 129) | 172 |
| | CIEDPSQAPDC (SEQ ID NO: 130) | 128 |
| | CEDPSQAPDAC (SEQ ID NO: 131) | 132 |

From the above results, it was confirmed that the huAbF46 antibodies were not able to bind to the SEMA domain of c-Met with the E168D mutation. This indicates that the antibodies may be used in a diagnosis method for providing cancer development information.

3) Analysis of Epitope Mapping Results of huAbF46

Figure 16:
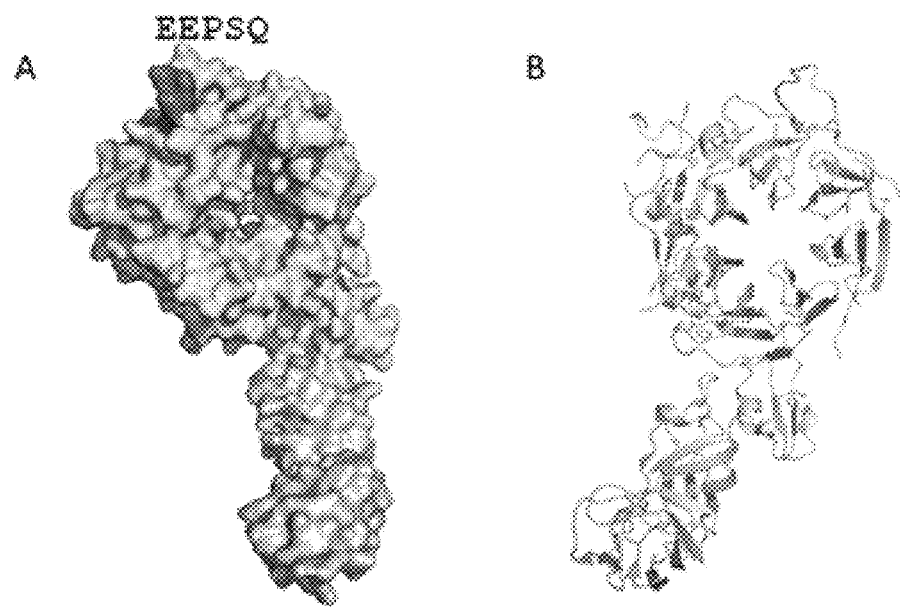

From the results shown above, it was confirmed that the huAbF46 antibodies specifically bound to both the linear and CLIPS peptides including the EEPSQ peptides consisting of 168th to 171st amino acids of c-Met protein without a non-specific reaction. This indicates that the huAbF46 antibodies bind to both the linear and conformational epitopes of c-Met protein. In terms of molecular structures (PyMOL 1.4.1 (www.pymol.org), Cn3D 4.1 (NCBI)), as illustrated in FIG. 16, it was confirmed that an epitope of huAbF46 was located at a SEMA domain. In addition, it was confirmed that a binding site of HGF was a position corresponding to a loop close to a direct binding site.

(2) Analysis of Full Positional Scanning Results

Each amino acid region of the EEPSQ sequence was substituted with 20 amino acids rather than the original amino acids, and any change that occurred in the binding affinity between each peptide and huAbF46 antibody was analyzed through 7 peptide arrays.

As a result of the analysis, it was confirmed which amino acid of the amino acid sequences of the EEPSQ sequence played a key role in binding with the antibody. In particular, it was confirmed that the EEP sequence in EEPSQ played a very critical role in binding with the antibody.

1.10 Analysis of Binding Affinity of huAbF46 Antibody by SEMA Domain Mutation

Each amino acid region or the total number of 5 amino acids of the EEPSQ sequence (SEQ ID NO: 73) was substituted with alanine rather than the original amino acid, and a binding affinity between each peptide ('AAAAA', 'AEPSQ', 'EAPSQ', 'EEASQ', 'EEPSQ', 'EEPSA', SEQ ID NO:132 through SEQ ID NO:137) and the huAbF46 antibody was measured using Biacore (GE healthcare). About 80 to 110 RU of the huAbF46 antibodies were immobilized on a CM5 chip, and 100 nM to 0.39 nM of the peptides having amino acid sequences of SEQ ID NOS: 132 through 137 were injected thereto at a rate of 30 μl/min in 9 different concentrations, thereby obtaining $k_{on}$ and $k_{off}$ values as shown in Table 4 below, and $K_D$ values were calculated therefrom. As a result, it was confirmed that the huAbF46 antibodies were not able to bind to the peptides with the substituted amino acids. From this result, the EEPSQ sequence was confirmed to be an essential epitope of the huAbF46 antibodies.

TABLE 4

| Antibody | Antigen | $k_{off}$ (1/Ms) | $k_{on}$ (1/s) | $K_D$ (nM) |
|---|---|---|---|---|
| huAbF46 | EEPSQ (SEQ ID NO: 73) | $4.30 \times 10^5$ | $7.05 \times 10^{-4}$ | 1.64 |
| huAbF46 | AAAAA (SEQ ID NO: 132) | | Not bound | |
| huAbF46 | AEPSQ (SEQ ID NO: 133) | | Not bound | |
| huAbF46 | EAPSQ (SEQ ID NO: 134) | | Not bound | |
| huAbF46 | EEASQ (SEQ ID NO: 135) | | Not bound | |
| huAbF46 | EEPAQ (SEQ ID NO: 136) | $4.32 \times 10^5$ | $6.16 \times 10^{-4}$ | 1.43 |
| huAbF46 | EEPSA (SEQ ID NO: 137) | | Not bound | |

Reference Example 2

Preparation of Anti-EGFR scFv

An antibody against EGFR was prepared by inserting a $(G_4S)_3$ linker peptide between a heavy chain variable domain and a light chain variable domain based on the scFv sequence of an anti-EGFR antibody. Briefly, a DNA encoding the scFv of an anti-EGFR antibody was synthesized using an automated gene synthesis machine (entrusted to Bioneer Corporation) in such a way that a $(GGGGS)_3$ linker peptide-encoding DNA sequence was added between DNA sequences (SEQ ID NOS: 110 and 112) coding respectively for the heavy chain variable domain (SEQ ID NO: 109) and the light chain variable domain (SEQ ID NO: 111) of a humanized anti-EGFR antibody.

Separately, a primary mutant anti-EGFR scFv was constructed in the same manner as the scFv, with the exception that a substitution was made of I for F at position 51 and of S for Q at position 62 on the heavy chain variable domain (SEQ ID NO: 109) and of L for R at position 46 and of E for F at position 83 on the light chain variable domain (SEQ ID NO: 111). These mutations improved the thermal stability of the resulting antibody. Further, a secondary mutant anti-EGFR scFv was constructed by substituting C for the amino acids at position 44 on the heavy chain variable domain and at position 100 on the light chain variable domain. In detail, a secondary mutant anti-EGFR scFv (heavy chain variable domain: SEQ ID NO: 113; light chain variable domain: SEQ ID NO: 114) was prepared in the same manner as described above, with the exception that a substitution was made of I for F at position at position 51, of C for G at position 44, and of S for Q at position 62 on the heavy chain variable domain (SEQ ID NO: 109), and of L for R at position 46, of E for F at position 83, and of C for G at position 100 on the light chain variable domain (SEQ ID NO: 111). These mutations allowed for the introduction of a stable disulfide bond in the fragment, thus improving in vivo pharmacokinetics of the resulting antibody fragment. Amino acid positions in the antibodies were numbered according to the Kabat numbering system.

The resulting products, anti-EGFR scFv, primary and secondary mutant anti-EGFR scFv molecules were used to construct the following bispecific antibodies.

Reference Example 3

Preparation of Anti-Her2 scFv

An scFv fragment binding to Her2 was prepared by inserting a $(G_4S)_3$ linker peptide between a heavy chain variable domain and a light chain variable domain based on the scFv sequence of Trastuzumab (herceptin). Briefly, a DNA encoding the scFv of an anti-Her2 antibody was synthesized using an automated gene synthesis machine (entrusted to Bioneer Corporation) in such a way that a $(GGGGS)_3$ linker peptide-encoding DNA sequence was added between DNA sequences (SEQ ID NOS: 116 and 118) coding respectively for the heavy chain variable domain (SEQ ID NO: 115) and the light chain variable domain (SEQ ID NO: 117) of an anti-Her2 antibody (Herceptin).

<Amino acid sequence of the heavy chain variable domain of anti-Her2 antibody>

(SEQ ID NO: 115)

EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS

-continued
<DNA sequence coding for the heavy chain
variable domain of anti-Her2 antibody>
(SEQ ID NO: 116)
gaagttcagctggtggagtctggcggtggcctggtgcagccaggggctc actccgtttgtcctgtgcagcttctggcttcaacattaaagacacctata tacactgggtgcgtcaggcccggghaagggcctggaatgggttgcaagg atttatcctacgaatggttatactagatatgccgatagcgtcaagggccg tttcactataagcgcagacacatccaaaaacacagcctacctgcagatga acagcctgcgtgctgaggacactgccgtctattattgttctagatgggga ggggacggcttctatgctatggactactggggtcaaggaaccctggtcac cgtctcctcg <Amino acid sequence of the light chain
variable domain of anti-Her2 antibody>
(SEQ ID NO: 117)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKR

<DNA sequence coding for the light chain
variable domain of anti-Her2 antibody>
(SEQ ID NO: 118)
gatatccagatgacccagtccccgagctccctgtccgcctctgtgggcga tagggtcaccatcacctgccgtgccagtcaggatgtgaatactgctgtag cctggtatcaacagaaaccaggaaaagctccgaaactactgatttactcg gcatccttcctctactctggagtcccttctcgcttctctggttccagatc tgggacggatttcactctgaccatcagcagtctgcagccggaagacttcg caacttattactgtcagcaacattatactactcctcccacgttcggacag ggtaccaaggtggagatcaaacga The resulting anti-Her2 scFv was used to construct the following bispecific antibody.

Example 1

Construction of Bispecific Antibody 1.1. Construction of Anti-c-Met/Anti-EGFR Bispecific Antibody The anti-c-Met antibody 13-1Y IgG2 prepared in Reference Example 1 was fused at the C-terminus of Fc with the anti-EGFR scFv, or the primary or the secondary mutant anti-EGFR scFv prepared in Reference Example 2. The fusion process was conducted as follows.

A DNA fragment which had a nucleotide sequence corresponding to the heavy chain of the anti-c-Met antibody L3-1Y-IgG2, prepared in Reference Example 1, was inserted between the EcoRI and XhoI restriction sites of pcDNA™3.3-TOPO TA Cloning Kit (Cat no. 8300-01) in OptiCHO™ Antibody Express Kit (Cat no. 12762-019, Invitrogen) while a DNA fragment corresponding to the light chain was inserted into pOptiVEC™-TOPO TA Cloning Kit. Subsequently, the anti-EGFR scFv prepared in Reference Example 2 was fused to the C-terminus of Fc of the L3-1Y-IgG2 inserted into pcDNA™3.3 via a 10-mer linker peptide composed of $(G4S)_2$ to construct a vector for expressing a bispecific antibody.

This recombinant vector was amplified using a Qiagen Maxiprep kit (Cat no. 12662), and transiently expressed with the aid of Freestyle™ MAX 293 Expression System (invitrogen). The transient expression was conducted in 293 F cells which were cultured in suspension in the FreeStyle™ 293 Expression medium. One day before transient expression, the cells were seeded at a density of $5 \times 10^5$ cells/ml. When the cells were grown for 24 hrs to a density of $1 \times 10^6$ cells/ml, transient expression was achieved. They were transfected with the DNA preparations by a liposomal reagent method using the Freestyle™ MAX reagent (Invitrogen). Briefly, a DNA mix of the heavy chain DNA: the light chain DNA=1:1 in a 15 ml tube was added to 2 ml of OptiPro™ SFM (Invtrogen) (tube A) while 100 μl of Freestyle™ MAX reagent and 2 ml of OptiPro™ SFM were mixed in another 15 ml tube (tube B). After tube A was admixed with tube B, the admixture was incubated for 15 min, and slowly added to the cells prepared one day prior. Thereafter, the cells were cultured for 5 days at 37° C. and 80% humidity under an 8% $CO_2$ atmosphere in a 30 rpm incubator.

After centrifugation of the cells, 100 ml of each supernatant was purified using the AKTA Prime (GE Healthcare). In this regard, the supernatant was loaded at a flow rate of 5 ml/min on a Protein A column (GE healthcare, 17-0405-03) mounted in the AKTA Prime, followed by elution with an IgG elution buffer (Thermo Scientific, 21004). The PBS buffer change yielded purified anti-c-Met/anti-EGFR bispecific antibodies.

The anti-c-Met/anti-EGFR bispecific antibodies in which the anti-EGFR scFv, the primary mutant anti-EGFR scFv, or the secondary mutant anti-EGFR scFv, was fused to the C-terminus of the anti-c-Met antibody L3-1Y-IgG2 were designated ME-01, ME-03, and ME-03S, respectively.

The anti-c-Met/anti-EGFR bispecific antibody was analyzed for affinity for the two antigens (c-Met/EGFR) using a Biacore T100 instrument (GE). A human Fab capturer (GE Healthcare) was immobilized onto a CM5 chip (#BR-1005-30, GE) according to the manufacturer's instruction. Following capture of about 90-120 RU of ME03S, sensograms were recorded for injection of solutions of c-Met-Fc (#358-MT/CF, R&D Systems) or EGFR-Fc (#344-ER, R&D Systems) varying in concentration. The chip surface was regenerated by injecting a 10 mM Glycine-HCl solution (pH 1.5). For affinity evaluation, the data was fitted using the BIAevaluation software (GE Healthcare, Biacore T100 evaluation software).

The results are summarized in Table 5, below.

TABLE 5

| Antibody | Antigen | KD (nM) | Ka (1/Ms) | kd (1/s) |
| --- | --- | --- | --- | --- |
| ME03S | c-Met | 0.23 | $6.7 \times 10^5$ | $1.6 \times 10^{-4}$ |
|  | EGFR | 0.12 | $2.4 \times 10^5$ | $2.7 \times 10^{-5}$ |

As shown in Table 5, all of the anti-c-Met/anti-EGFR bispecific antibodies prepared in Example 1 bound both antigens.

1.2. Construction of Anti-c-Met/Anti-Her2 Bispecific Antibody

The anti-c-Met antibody 13-1Y IgG2 (uAbF46-H4-A1 (IgG2 Fc)) prepared in Reference Example 1 was fused at the C-terminus of Fc with the anti-Her2 scFv prepared in Reference Example 3. The fusion process was conducted as follows.

A DNA fragment which had a nucleotide sequence (SEQ ID NO: 66) corresponding to the heavy chain of the anti-c-Met antibody L3-1Y-IgG2, prepared in Reference Example 1, was inserted between the EcoRI and XhoI restriction sites of pcDNA™3.3-TOPO TA Cloning Kit (Cat no. 8300-01) in OptiCHO™ Antibody Express Kit (Cat no. 12762-019, Invitrogen) while a DNA fragment including a nucleotide sequence (SEQ ID NO: 68) corresponding to the light chain was inserted into pOptiVEC™-TOPO TA Cloning Kit. Subsequently, the anti-Her2 scFv-encoding DNA prepared in Reference Example 3 was fused to the C-terminus of Fc of the L3-1Y-IgG2 inserted into pcDNA™3.3 via a linker peptide composed of (GGGGS)$_2$ to construct a vector for expressing a bispecific antibody.

This recombinant vector was amplified using a Qiagen Maxiprep kit (Cat no. 12662), and transiently expressed with the aid of Freestyle™ MAX 293 Expression System (invitrogen). The transient expression was conducted in 293 F cells which were cultured in suspension in the FreeStyle™ 293 Expression medium. One day before transient expression, the cells were seeded at a density of 5×10$^5$ cells/ml.

When the cells were grown for 24 hrs to a density of 1×10$^6$ cells/ml, transient expression was achieved. They were transfected with the DNA preparation by a liposomal reagent method using the Freestyle™ MAX reagent (Invitrogen). Briefly, a DNA mix of the heavy chain DNA:the light chain DNA=3:2 in a 15 ml tube was added to 2 ml of OptiPro™ SFM (Invtrogen) (tube A) while 100 µl of Freestyle™ MAX reagent and 2 ml of OptiPro™ SFM were mixed in another 15 ml tube (tube B). After tube A was admixed with tube B, the admixture was incubated for 15 min, and slowly added to the cells prepared one day ago. Thereafter, the cells were cultured for 5 days at 37° C. and 80% humidity under an 8% CO$_2$ atmosphere in a 30 rpm incubator.

After centrifugation of the cells, 100 ml of the supernatant was purified using the AKTA Prime (GE Healthcare). In this regard, the supernatant was loaded at a flow rate of 5 ml/min on a Protein A column (GE healthcare, 17-0405-03) mounted in the AKTA Prime, followed by eluting with an IgG elution buffer (Thermo Scientific, 21004). The PBS buffer change yielded a purified anti-c-Met/anti-Her2 bispecific antibody.

The anti-c-Met/anti-Her2 bispecific antibody in which the anti-Her2 scFv was fused to the C-terminus of the anti-c-Met antibody L3-1Y-IgG2 was designated MH2-01.

The anti-c-Met/anti-Her2 bispecific antibody was analyzed for affinity for the two antigens (c-Met/Her2) using a Biacore T100 instrument (GE). A human Fab capturer (GE Healthcare) was immobilized onto a CM5 chip (#BR-1005-30, GE) according to the manufacturer's instruction. Following capture of about 90-120 RU of MH2-01, sensograms were recorded for injection of solutions of c-Met-Fc (#358-MT/CF, R&D Systems) or Her2-Fc (1129-ER, R&D Systems) varying in concentration. The chip surface was regenerated by injecting a 10 mM Glycine-HCl solution (pH 1.5). For affinity evaluation, the data was fitted using the BIAevaluation software (GE Healthcare, Biacore T100 evaluation software).

The results are summarized in Table 6, below

TABLE 6

| Antibody | Antigen | $K_D$ (nM) | $k_a$ (1/Ms) | $k_d$ (1/s) |
|---|---|---|---|---|
| MH2-01 | cMet | 0.14 | 6.6 × 10$^5$ | 9.3 × 10$^{-5}$ |
|  | Her2 | <0.01 | 1.2 × 10$^5$ | <1.1 × 10$^{-5}$ |

As shown in Table 6, all of the anti-c-Met/anti-EGFR bispecific antibodies prepared in Example 1 according to an embodiment bound both the two antigens.

Example 2

Bispecific Antibody-Induced c-Met Degradation

The anti-c-Met/anti-EGFR bispecific antibody and the anti-c-Met/anti-Her2 bispecific antibody respectively prepared in Examples 1.1 and 1.2 were assayed for inhibitory activity against cancer cell growth in the stomach cancer cell line MKN45.

All cell lines were cultured in RPMI1640 (#11875-093, Gibco) supplemented with 10% (v/v) FBS and 1% (v/v) Penicilin-Streptomycin at 37° C. in a 5% CO$_2$ atmosphere.

Effects of the bispecific antibodies prepared in Examples 1.1 and 1.2 on the degradation of the c-Met protein were evaluated by measuring a relative total amount of c-Met. The relative total amount of c-Met reflected a change in the total amount of c-Met as a result of antibody-triggered internalization into a cell and degradation of c-Met, thus evaluating the efficacy of the antibodies.

The stomach cancer cell line MKN45 (Japanese Cancer Research Bank (JCRB), Tokyo, Japan) was seeded at a density of 2×10$^5$ cells/ml, together with each antibody (5 µg/ml), to 96-well plates, and incubated for 24 hrs. After lysis of the antibody-treated cells, a change in the total amount of c-Met was measured using a Human total HGF R/c-Met ELISA KIT (R&D systems, DYC358).

Figure 4:
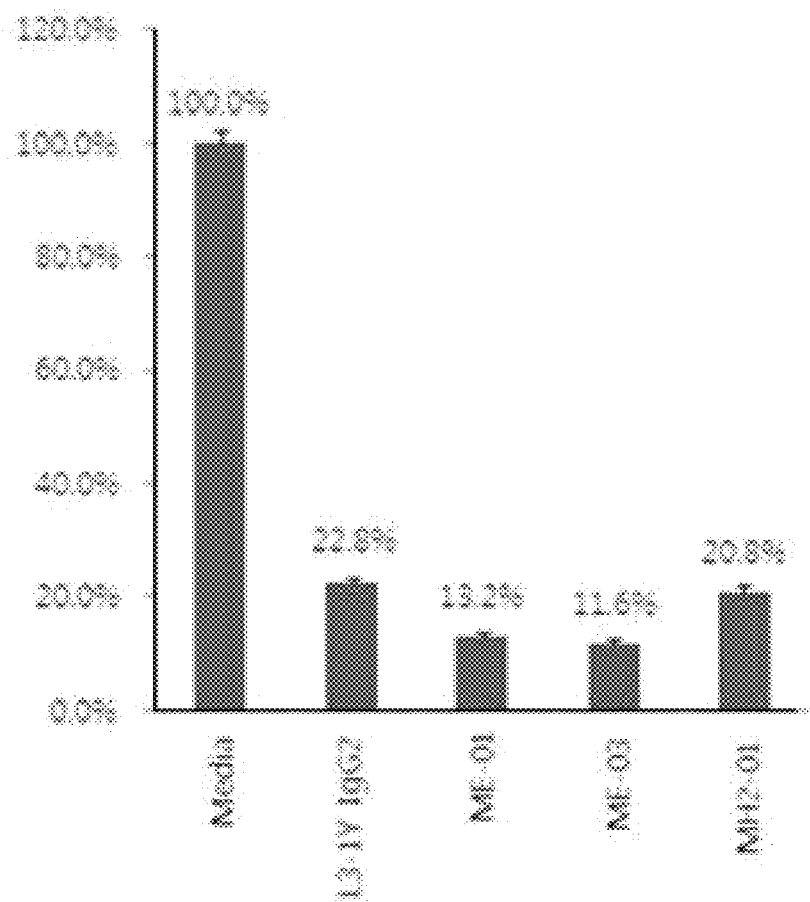
FIG. 4 is a graph illustrating the activity of the anti-c-Met/anti-EGFR bispecific antibody against degraded c-Met in MKN45 stomach cancer cells (Y-axis: relative level of c-Met to the control (media); X-axis: L3-1Y IgG2: anti-c-Met antibody, ME-01 and ME-03: anti-c-Met/anti-EGFR bispecitic antibodies, MH2-01: anti-c-Met/anti-HER2 bispecific antibody).

The results are depicted in FIG. 4. As can be seen in the graph of FIG. 4, the anti-c-Met/anti-EGFR bispecific antibodies ME-01 and ME-03 were observed to degrade c-Met by 86.8% and 88.4%, respectively, in the MKN45 stomach cancer cells, which overexpress c-Met. Also, c-Met was about 80% degraded when treated with the anti-c-Met/anti-Her bispecific antibody MH2-01. Compared to the anti-c-Met antibody L3-1Y or L3-1Y IgG2, the bispecific antibodies were significantly improved in c-Met degradation activity. Taken together, the data suggest that the anti-c-Met antibody acts to degrade c-Met in synergy with the anti-EGFR or anti-Her2 antibody (scFv) when they were fused together.

Example 3

Anti-c-Met/Anti-EGFR Bispecific Antibody-Induced Internalization and Degradation of EGFR MKN45 cells (Japanese Cancer Research Bank (JCRB), Tokyo, Japan) were seeded at a density of 2×10$^4$ cells/well into 96-well plates, and incubated at 37° C. for 4 hrs with L3-1Y-IgG2 (Reference Example 1), an anti-EGFR antibody (see infra), and the anti-c-Met/anti-EGFR bispecific antibody ME-03 (Example 1.1), individually or in combination. Each antibody was used at a density of 5 µg/ml/well, whether individually or in combination. For control, the cells were treated with PBS only. The cells were immobilized onto the plates by treatment with 4% (v/v) formaldehyde for 15 min, washed three times with PBS, and then blocked with a blocking buffer (0.5% triton x-100 and 5% donkey serum) at room temperature for 1 hr. To each well, 100 µl of a 1:100 dilution of each of primary antibodies to c-Met (FAB3582A, R&D systems) and EGFR (#5616, Cell signaling) was added, and incubated for 15 hrs at 4° C. The cells were washed again three times with PBS, and incubated at room temperature for 1 hr with 100 µl of a 1:2000 dilution of a secondary antibody (A21433, Invitrogen). After being washed three times with PBS, the cells were counterstained with a DAPI-containing mounting medium (H-1200, Vector Lab), and examined by Confocal microscopy (Zeiss, LSM710).

The anti-EGFR antibody was a scFv-Fc antibody recognizing EGFR and was constructed by fusing the heavy chain variable domain of SEQ ID NO: 109 and the light chain variable domain of SEQ ID NO: 111, both shown in Reference Example 2, to the N-terminus of IgG2 Fc.

Figure 5:
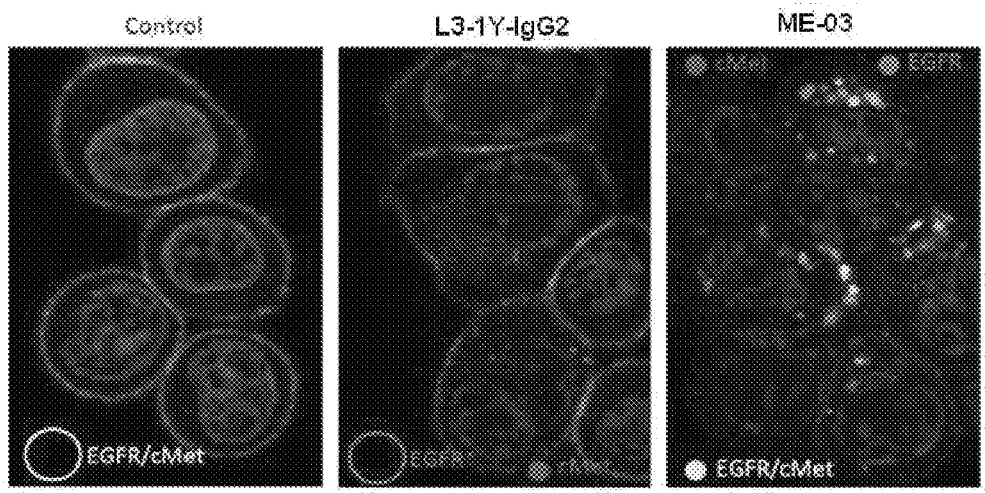
FIG. 5 are fluorescent images showing the anti-c-Met/anti-EGFR bispecific antibody-induced degradation of EGFR in MKN45 stomach cancer cells (yellow: anti-c-Met/anti-EGFR bispecific antibody; red: anti-c-Met antibody; green: anti-EGFR antibody).

The results are shown in FIG. 5. As can be seen in the confocal microimages of FIG. 5, the anti-c-Met/anti-EGFR bispecific antibody caused the target membrane protein EGFR to undergo internalization into a cell and degradation in the cells which overexpressed c-Met on the plasma membrane (right panel). In contrast, the internalization of EGFR was not observed in the presence of the anti-c-Met antibody alone. Likewise, treatment with the anti-EGFR antibody did not provoke the degradation of EGFR at all. These results indicate that the anti-c-Met/anti-EGFR bispecific antibody can trigger the internalization into a cell and degradation of the EGFR located in the plasma membrane.

Comparison was made of degradation efficiency between the bispecific antibody and a combination of the monospecific antibodies. The anti-EGFR antibody (anti-EGFR ab), the L3-1Y-IgG2 (Reference Example 1), and the anti-c-Met/anti-EGFR bispecific antibody ME-03 (Example 1.1) were applied to each well at a density of 5 µg/ml, individually or in combination (in this case, each 5 µg/ml, too), and the same experiment to obtain the results of FIG. 5 was performed.

Figure 6:
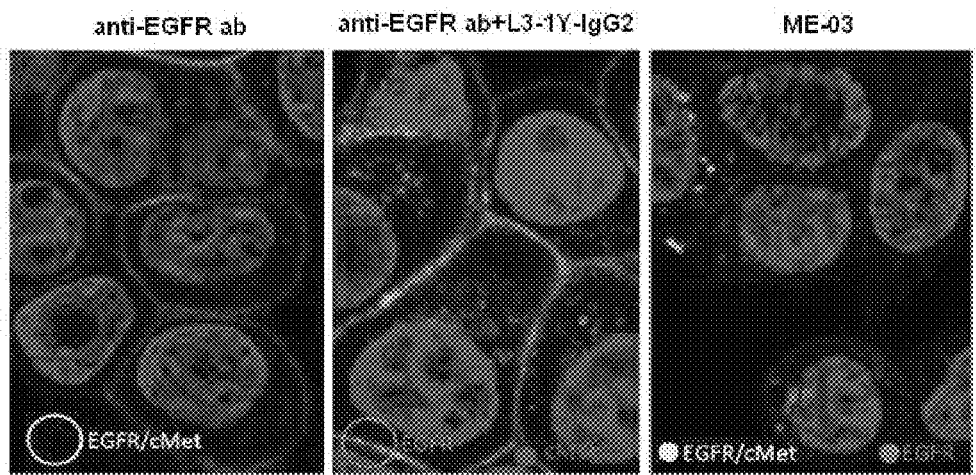
FIG. 6 are fluorescent images comparing the internalization into a cell and degradation of EGFR between MKN45 stomach cancer cells treated with the anti-c-Met/anti-EGFR bispecific antibody and cells treated with an anti-EGFR antibody (ICR62) alone or in combination with an anti-c-Met antibody (yellow: anti-c-Met/anti-EGFR bispecific antibody; red: anti-c-Met antibody; green: anti-EGFR antibody).

Results are given in FIG. 6. As shown in FIG. 6, the anti-c-Met/anti-EGFR antibody bispecific antibody (ME-03) could trigger the internalization into a cell and degeneration of EGFR whereas a combination of individual anti-c-Met and the anti-EGFR antibodies could not. These results indicate that the internalization into a cell and degradation of EGFR is accounted for by the operation of a membrane protein depletion system in which the anti-c-Met/anti-EGFR bispecific antibody (ME-03) triggers c-Met to act as a driver while holding the EGFR. No changes were detected in the position of EGFR in the cells when individual antibodies were used in combination. The anti-c-Met antibody (L3-1Y-IgG2) was observed to cause only c-Met to be internalized into a cell and degraded.

When MKN45 stomach cancer cells were treated with various anti-c-Met antibodies and anti-EGFR antibodies alone or in combination, or with the anti-c-Met/anti-EGFR bispecific antibody, locations of the membrane proteins (EGFR and c-Met) in the cells were monitored.

Briefly, the anti-EGFR antibody (anti-EGFR ab), L3-1Y-IgG2 (Reference Example 1), ERBITUX® (cetuximab) (#ET509081213, Merck) and the anti-c-Met/anti-EGFR bispecific antibody ME-03S (Example 1.1) were applied to each well at a density of 5 µg/ml, individually or in combination (in this case, each 5 µg/ml, too), and the same experiment to obtain the results of FIG. 5 was performed.

Figure 7:
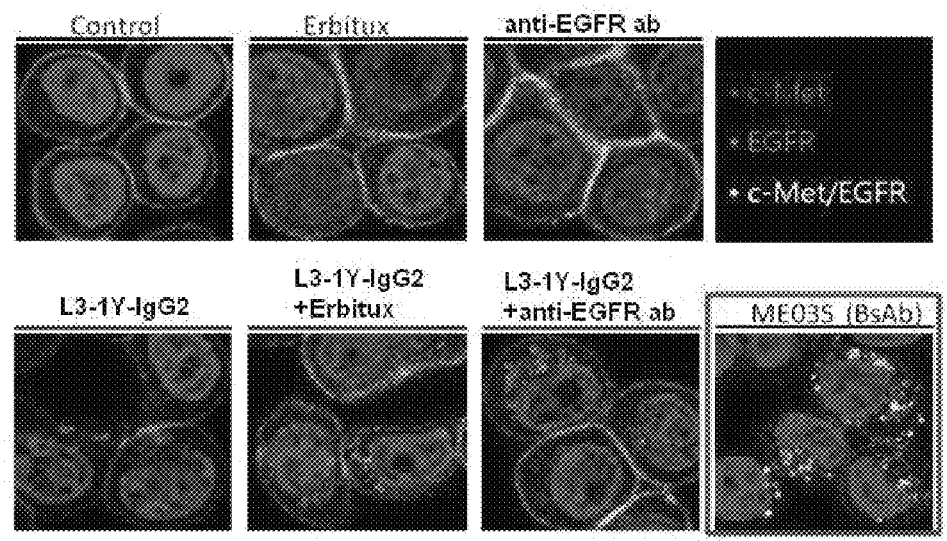
FIG. 7 are fluorescent images comparing the internalization into a cell and degradation of EGFR between MKN45 stomach cancer cells treated with the anti-c-Met/anti-EGFR bispecific antibody and cells treated with an anti-c-Met antibody alone or in combination with an anti-EGFR antibody (ICR62 or ERBITUX® (cetuximab) (yellow: anti-c-Met/anti-EGFR bispecific antibody; red: anti-c-Met antibody; green: anti-EGFR antibody).

Results are given in FIG. 7. As shown in FIG. 7, the internalization of EGFR was induced by neither the anticancer agent ERBITUX® (cetuximab) nor the scFV-Fc antibody anti-EGFR ab, both recognizing EGFR, but could be induced by the anti-c-Met/anti-EGFR bispecific antibody (ME-03S).

The anti-c-Met/anti-EGFR bispecific antibody-induced internalization into a cell and degradation of EGFR was examined in another different cancer cell line, e.g., EBC-1 lung cancer cell line (JCRB, Japanese Collection of Research Bioresources).

Briefly, the anti-EGFR antibody (anti-EGFR ab), L3-1Y-IgG2 (Reference Example 1), Herceptin (Roche), the anti-c-Met/anti-EGFR bispecific antibody ME-03S (Example 1.1), and the anti-c-Met/anti-Her2 bispecific antibody MH2-01 (Example 1.2) were applied at a density of 5 µg/ml to each well, individually or in combination (in this case, each 5 µg/ml, too), and the same experiment to obtain the results of FIG. 5 was performed.

Figure 8:
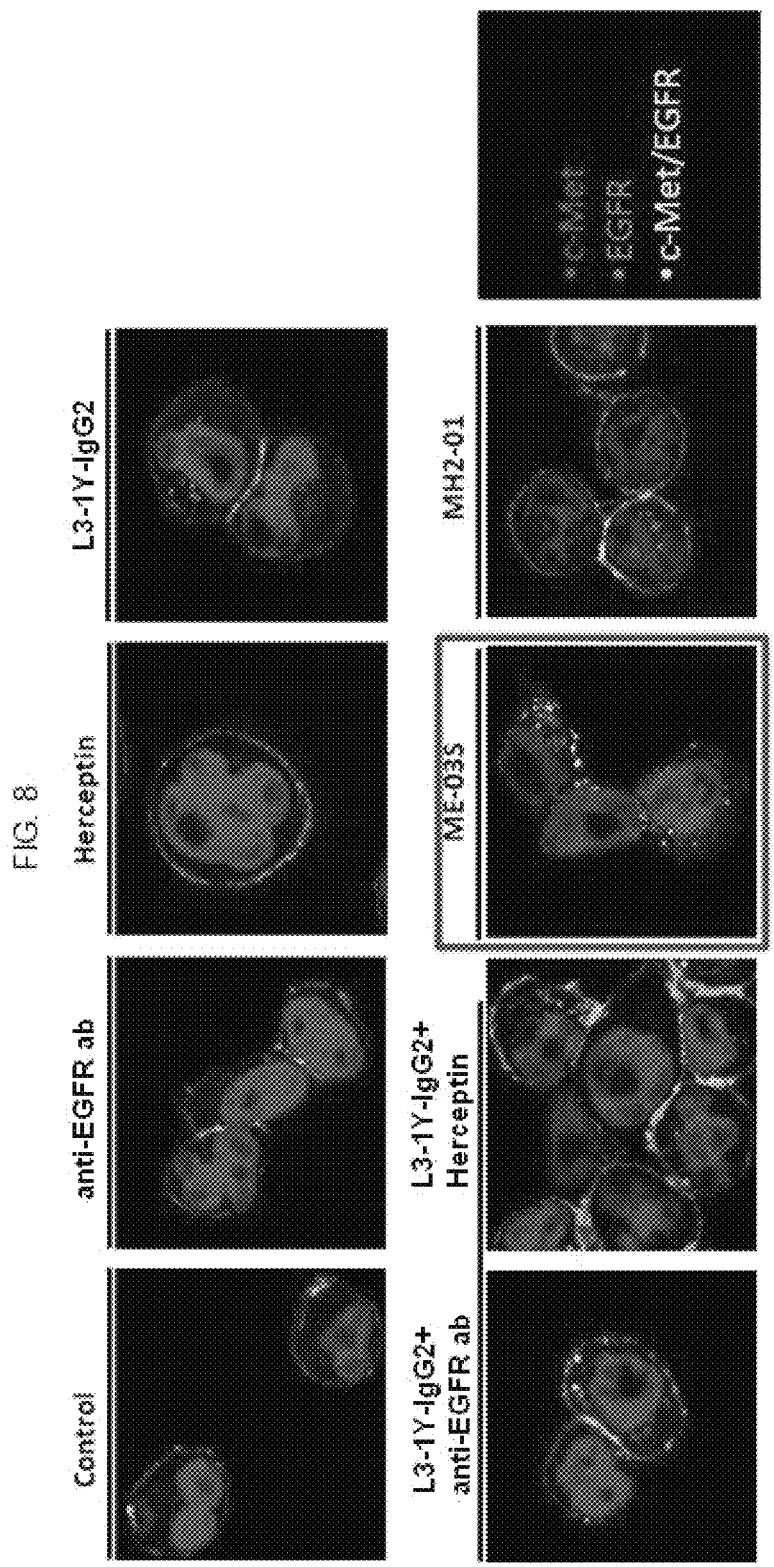
FIG. 8 are fluorescent images comparing the internalization into a cell and degradation of EGFR between MKN45 stomach cancer cells treated with the anti-c-Met/anti-EGFR bispecific antibody and cells treated with an anti-c-Met antibody or an anti-EGFR antibody (ICR62 or ERBITUX® (cetuximab)) alone, or a combination thereof (yellow: anti-c-Met/anti-EGFR bispecific antibody; red: anti-c-Met antibody; green: anti-EGFR antibody).

Results are given in FIG. 8. As shown in FIG. 8, the lung cancer cell line, like the stomach cancer cell line, allowed for the internalization of EGFR only by treatment with anti-c-Met/anti-EGFR bispecific antibody (ME-03S). MH2-01, although a bispecific antibody, had no influences on EGFR, but induced only the target Her2 to undergo internalization/degradation. These results indicate the EGFR-specific depletion of the anti-c-Met/anti-EGFR bispecific antibody (ME-03S).

Further, the anti-c-Met/anti-EGFR bispecific antibody-induced specific internalization into a cell and degradation of EGFR was evaluated by measuring a total amount of EGFR and a change in EGFR activity after treatment with the anti-c-Met/anti-EGFR bispecific antibody (ME-03). In this regard, a total level of EGFR and a change in EGFR activity were examined by Western blotting analysis (with phosphorylated-EGFR) after the MKN45 stomach cancer cell line and the EBC-1 lung cancer cell line were treated for 24 hrs with the anti-c-Met/anti-EGFR bispecific antibody (ME-03).

Briefly, MKN45 cells (Japanese Cancer Research Bank (JCRB), Tokyo, Japan) and EBC-1 cells (JCRB Japanese Collection of Research Bioresources) were grown in triplicate in 96-well plates (5000~10,000 cells per well), and incubated for 24 hrs with 1 µM geftinib (#S1025, Selleckchem), 5 µg/ml ERBITUX® (cetuximab) (#ET509081213, Merck), 5 µg/ml L3-1Y-IgG2 (Reference Example 1), or 5 µg/ml the anti-c-Met/anti-EGFR bispecific antibody ME-03 (Example 1.1). EGF was added at a density of 100 ng/ml 30 min before cell lysis.

Western blotting results are given in FIG. 9. As is apparent from the data of FIG. 9, both MKN45 and EBC-1 cells were decreased in EGFR activity, but exhibited no changes in the total level of EGFR when they were treated with the EGFR inhibitor Gefitinib or the anti-EGFR antibody ERBITUX® (cetuximab) alone. In contrast, the anti-c-Met/anti-EGFR bispecific antibody (ME-03) caused both of the cancer cell lines to significantly decrease in both the EGFR activity and the total level of EGFR, resulting in complete degradation of EGFR after 24 hrs of treatment.

Example 4

Assay for Anti-c-Met/Anti-EGFR Bispecific Antibody-Induced Depletion of EGFR in Cell with Low c-Met Expression An examination was made to see whether the anti-c-Met/anti-EGFR bispecific antibody can deplete the membrane protein EGFR even in the cells where c-Met, serving as a driver, is expressed at a low level. In this context, A431 cells (American Type Culture Collection (ATCC) CRL-1555) which express a low level of c-Met, were incubated with the anti-c-Met/anti-EGFR bispecific antibody (ME-03) prepared in Example 1.1, and the depletion of EGFR was analyzed by Western blotting. A431 cells express EGFR at a very high level, but c-Met at a very low level, and are extensively used for studying EGFR functions. Thus, the cells are far more abundant in EGFR than c-Met, which serves as a driver.

Briefly, MKN45 and EBC-1 cells were grown in triplicate in 96-well plates ($2 \times 10^5$ cells/ml), and then incubated for 24 hrs with 5 µg/ml ERBITUX® (cetuximab) (#ET509081213, Merck), 5 µg/ml L3-1Y-IgG2 (Reference Example 1; L3-1Y in FIG. 10), and 5 µg/ml of the anti-c-Met/anti-EGFR bispecific antibody ME-03 (Example 1.1) alone or in combination (in this case, each 5 µg/ml, too). EGF was added at a density of 100 ng/ml 30 min before cell lysis. Subsequently, the cells treated with the antibodies were lyzed, and measured for change in the total amount of c-Met, and EGFR phosphorylation using Human total HGF R/c-MET ELISA KIT (R&D systems, DYC358) and phosphor-EGFR.

The results are given in FIG. 10. As is apparent from the data of FIG. 10, the anti-c-Met/anti-EGFR bispecific antibody (ME-03) inhibited the phosphorylation of EGFR thanks to its anti-EFGR scFv component which targets EGFR, but could not decrease the total amount of EGFR. These results imply that the bispecific antibody cannot induce the degradation of the target membrane protein when c-Met, serving as a driver, is not present at a sufficient level. Hence, a certain level of the driver protein is required for the bispecific antibody to induce the degradation of membrane proteins.

Example 5

Assay for Anti-c-Met/Anti-EGFR Bispecific Antibody-Induced Depletion of EGFR in c-Met-Expressed Cells The effect of expression levels of c-Met on the anti-c-Met/anti-EGFR bispecific antibody-induced degradation of EGFR was evaluated.

After HCC827 lung cancer cells were treated with the anti-c-Met/anti-EGFR bispecific antibody (ME-03S), the degradation of the target membrane protein EGFR was measured by Western blot analysis. Reference was made to Example 4 for experiment procedures. Wild-type HCC827 lung cancer cells (HCC827 WT cells; American Type Culture Collection (ATCC) CRL-2868) and Erlotinib-resistant HCC827 lung cancer cells (HCC827 ER#15 cells; while HCC827 WT cells (American Type Culture Collection, ATCC CRL-2868) were cultured in the presence of Erlotinib (#S1023, Selleckchem) varying in concentration from 5 nM to 2 µM and cells resistant to Erlotinib were selected. Of them, clones with increased c-Met expression levels were further selected and were employed. Each antibody was used as shown in FIG. 11 (in FIG. 11, L3-1Y represents L3-1Y-IgG2 (Reference Example 1)).

The results are given in FIG. 11. HCC827 WT cells express EGFR at a very high level, but c-Met at a very low level, and are extensively used for studying the function of the EGFR inhibitor Erlotinib. Thus, the cells are far more abundant in EGFR than c-Met, which serves as a driver. In the HCC827 WT cells, as seen in FIG. 11, the anti-c-Met/anti-EGFR bispecific antibody (ME-03S) decreased the phosphorylation of EGFR, but did not reduce the total amount of EGFR.

HCC827 ER#15 cells are resistant to Erlotinib, with a concomitant increase in the expression level and activity of c-Met. In the HCC827 ER#15 cells, as is understood from FIG. 1, the anti-c-Met/anti-EGFR bispecific antibody (ME-03S) inhibited the phosphorylation of EGFR, and decreased the total amount of EGFR with an increase in the expression level of c-Met which served as a driver. These data indicate that the bispecific antibody-induced degradation of target membrane proteins is dependent on the level of the driver (c-Met) in the plasma membrane.

Example 6 c-Met/Her2 Bispecific Antibody-Induced Specific Degradation of HER2

The activity of the system for target membrane protein depletion was directed toward a different target: HER2 in MKN45 stomach cancer cells. In this context, the anti-c-Met/anti-EGFR bispecific antibody (ME-02; Example 1.1) and the anti-c-Met/anti-Her2 bispecific antibody (MH2-01S; Example 1.2) were employed in the system.

MKN45 cells were treated with the anti-c-Met/anti-EGFR bispecific antibody MH2-01S or the anti-c-Met/anti-Her2 bispecific antibody ME-03, and measured for HER2 level by Western blot analysis.

Briefly, MKN45 and EBC-1 cells were grown in triplicate in 96-well plates ($2 \times 10^5$ cells/ml), and then incubated for 24 hrs with ERBITUX® (cetuximab) (#ET509081213, Merck), Herceptin (Roche), L3-1Y-IgG2 (Reference Example 1), the anti-c-Met/anti-EGFR bispecific antibody ME-03 (Example 1.1), or the anti-c-Met/anti-Her2 bispecific antibody MH2-01 (Example 1.2), each 5 µg/ml. EGF was added at a density of 100 ng/ml 30 min before cell lysis. Subsequently, the cells treated with the antibodies were lysed, and measured for change in the total amount of c-Met, and EGFR phosphorylation using Human total HGF R/c-MET ELISA KIT (R&D systems, DYC358) and phosphor-EGFR.

The results are given in FIG. 12. As is apparent from the data of FIG. 12, the MKN45 stomach cancer cells, in which c-Met, serving as a driver, was overexpressed, were observed to internalize and degrade the target membrane protein HER upon treatment with the anti-c-Met/anti-HER2 bispecific antibody (MH2-01S), whereas no changes in HER2 expression level were detected when the cells were treated with the anti-c-Met/anti-EGFR bispecific antibody ME-03. Because MH2-01S had no influences on EGFR as shown in FIG. 8, the antibody was understood to trigger the specific internalization into a cell and degradation of HER2 only. Therefore, these data indicate that the system for membrane protein depletion (bispecific antibody) targets proteins of interest specifically.

Example 7

Anti-c-Met/Anti-EGFR Bispecific Antibody-Induced Degradation of EGFR Following c-Met Overexpression The technical applicability of the system of target membrane protein depletion in accordance with an embodiment was examined. To this end, after c-Met was artificially overexpressed in A549 lung cancer cells (pleniMet transfected cells), a system for membrane protein depletion (anti-c-Met/anti-EGFR bispecific antibody ME-03S) was applied to the cells which were then monitored for EGFR degradation by fluorescence microscopy.

Briefly, A549 cells (American Type Culture Collection (ATCC) CRL-185) were seeded at a density of $2 \times 10^4$ cells/well, together with a mixture of Fugene6 transfection reagent (Invitrogen Lipofectamine™ 2000) and plentic-Met vector (SMC, Samsung Medical Center) into well plates, followed by incubation for 24 hrs for transfection through reverse transcription (performed using 0.1-3.0 µg/µl DNA in Opti-MEM according to the manufacturer's instruction). Then, the cells were treated for 4 hrs at 37° C. with L3-1Y-IgG2 (Reference Example 1), the anti-EGFR ab (Example 3), and the anti-c-Met/anti-EGFR bispecific antibody ME03S (Example 1.1) individually or in combination (each, 1 µg/ml/well, even in combination). The cells were immobilized onto the plates by treatment with 4% (v/v) formaldehyde for 15 min, washed three times with PBS, and then blocked with a blocking buffer (0.5% triton x-100 and 5% donkey serum) at room temperature for 1 hr. To each well, 100 µl of a 1:100 dilution of each of primary antibodies to c-Met (37-0100, Invitrogen) and EGFR (#5616, Cell signaling) was added, and incubated for 15 hrs at 4° C. The cells were washed again three times with PBS, and incubated at room temperature for 1 hr with 100 µl of a 1:1000 dilution of a secondary antibody (A21433, Invitrogen). After being washed three times with PBS, the cells were counterstained with a DAPI-containing mounting medium (H-1200, Vector Lab), and examined by Confocal microscopy (Zeiss, LSM710).

The results are shown in FIG. 13. The last panel in FIG. 13 is a separate green image of the ME03S-treated cells so as to clearly visualize the internalization of EGFR because the confocal images of the cells were too strong in red to discriminate the pattern of green signals. As can be seen in FIG. 13, when cells were artificially allowed to overexpress the driver (c-Met) in the plasma membrane, the anti-c-Met/anti-EGFR bispecific antibody ME-03S was found to induce the internalization into a cell and degradation of EGFR. These data indicate that the system for membrane protein depletion can specifically deplete target membrane proteins, depending on the kind of the trigger.

Referring to the experiment procedure for the data of FIG. 13, a system for membrane protein depletion [anti-c-Met/anti-EGFR bispecific antibody ME-03S (Example 1.1) or anti-c-Met/anti-HER2 bispecific antibody MH2-01 (Example 1.2)] was applied to HeLa cells (CCL-2, ATCC) in which c-Met had been artificially overexpressed (plenti::c-Met transfected cell), and was monitored for the degradation of EGFR by fluorescence microscopy.

The results are given in FIG. 14 wherein 'low exposure' and 'high exposure' represent different signal intensities, and are fluorescence images at low gain values and at high gain values, respectively. High gain values could help visualize c-Met signals (red) even in the cells of low fluorescence. As can be seen in FIG. 14, the anti-c-Met/anti-EGFR bispecific antibody (ME03S) was found to trigger EGFR to undergo internalization into a cell and degradation in the cells in which the driver (c-Met) was artificially overexpressed. In contrast, the anti-c-Met/anti-HER2 bispecific antibody MH2-01 could not trigger the internalization into a cell and degradation of EGFR because it is a trigger for the membrane protein HER2. Taken together, the data indicate that the system for membrane protein depletion in accordance with the present invention can specifically target and degrade membrane proteins of interest, depending on the type of the trigger.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of target membrane protein depletion, the method comprising
   treating a cell with a dual binding molecule comprising a first binding domain which binds to a driver membrane protein on the cell surface and a second binding domain which binds to a target membrane protein on the cell surface, wherein
   the driver membrane protein is c-Met;
   the first binding domain is an anti-c-Met antibody or antigen-binding antibody fragment thereof that specifically binds to an epitope comprising 5 or more contiguous amino acids within the SEMA domain of c-Met protein comprising the amino acid sequence of SEQ ID NO: 73;
   and the second binding domain is an antibody, antigen-binding antibody fragment, or DARPin;
   and
   wherein the driver membrane protein and target membrane protein are internalized into the cell and degraded when the first binding domain of the dual binding molecule binds the driver membrane protein and the second binding domain binds the target membrane protein.

2. The method of target membrane protein depletion according to claim 1, wherein the target membrane protein is selected from the group consisting of a receptor, a channel protein, a membrane enzyme, a lipoprotein, an integrin, and a marker on a cell surface, and the driver membrane protein is internalized by interaction with the anti-c-Met antibody or antigen-binding antibody fragment.

3. The method of target membrane protein depletion according to claim 2, wherein the target membrane protein is selected from the group consisting of a receptor tyrosine kinase (RTK), a G-protein-coupled receptor (GPCR), a transferrin receptor, a low-density lipoprotein (LDL) receptor, and a cluster of differentiation (CD), tetraspanins, and membrane targets for antibody drug conjugates (ADC).

4. The method of target membrane protein depletion according to claim 3, wherein the target membrane protein is selected from the group consisting of an epidermal growth factor receptor (EGFR), a vascular endothelial growth factor receptor (VEGFR), HER2 protein (Human Epidermal growth factor Receptor 2 protein), HER3 protein (Human Epidermal growth factor Receptor 3 protein), a platelet-derived growth factor receptor (PDGFR), CD9, CD81, CD151, CD63, CD37, CD53, NET1, NET2, NET4, NET5, NET6, TM4SF6, Tspan2, Tspan3, TM4B, CD22, CD79b, CD22, GPNMB, CD19, CD56, CD138, PSMA, EGFR, CD74, TACSTD2, CEA, Folate receptor 1, CD37, Mucin16, ETB, STEAP1, CD70, SLC44A4, Nectin4, AGS-16, Guanylyl cyclase C, Mucin1, EGFRvIII, and Mesothelin.

5. The method of target membrane protein depletion according to claim 1, wherein the dual binding molecule is a bispecific antibody comprising the first and second binding domains, and
   the first binding domain is an anti-c-Met antibody or an antigen-binding fragment thereof, and
   the second binding domain is an antibody against the target membrane protein or an antigen-binding fragment thereof.

6. The method of target membrane protein depletion according to claim 1,
wherein the anti-c-Met antibody or the antigen-binding fragment thereof specifically binds to an epitope comprising 5 to 19 contiguous amino acids of SEQ ID NO: 71 comprising the amino acid sequence of SEQ ID NO: 73.

7. The method of target membrane protein depletion according to claim 6,
wherein the anti-c-Met antibody or the antigen-binding fragment thereof comprises:
(a) a CDR-H1 comprising the amino acid sequence of SEQ ID NO: 4; (b) a CDR-H2 comprising the amino acid sequence of SEQ ID NO: 5 or SEQ ID NO: 2; (c) a CDR-H3 including the amino acid sequence of SEQ ID NO: 6, or SEQ ID NO: 3;
(d) a CDR-L1 comprising the amino acid sequence of SEQ ID NO: 7, (e) a CDR-L2 comprising the amino acid sequence of SEQ ID NO: 8, and (f) a CDR-L3 comprising the amino acid sequence of SEQ ID NO: 9, SEQ ID NO: 86, or an amino acid sequence comprising 9-17 consecutive amino acids of SEQ ID NO: 89 including the $1^{st}$ to $9^{th}$ positions of SEQ ID NO: 89.

8. The method of target membrane protein depletion according to claim 1, wherein the first binding domain is an anti-c-Met antibody and the second binding domain is an scFv, $(scFv)_2$, Fab, Fab', F(ab')2, or antibody mimic that binds to the target membrane protein, which is linked to the c-terminus of the antibody that binds to the driver membrane protein.

9. The method of target membrane protein depletion according to claim 1, wherein the first binding domain is an anti-c-Met antibody and the second binding domain is an anti-EGFR antibody, an anti-HER2 antibody, an anti-HER3 antibody, an anti-VEGFR antibody, an anti-PDGFR antibody, an anti-IGF-1R antibody, or an antigen-binding fragment thereof.

10. The method of target membrane protein depletion according to claim 9, wherein
the anti-EGFR antibody is cetuximab, panitumumab, matuzumab, necitumumab, nimotuzumab, zalutumumab, MM-151, or an antibody comprising a heavy chain variable region comprising the amino acid sequence of SEQ ID NO: 109 or SEQ ID NO: 111 and a light chain variable region comprising the amino acid sequence of SEQ ID NO: 110 or SEQ ID NO: 112,
the anti-HER2 antibody is trastuzumab or pertuzumab,
the anti-HER3 antibody is RG-7597,
the anti-VEGFR antibody is ramucirumab,
the anti-PDGFR antibody is olaratumab, and
the anti-IGF-1R antibody is cixutumumab.

11. The method of claim 1, wherein the cell is in a subject and the cell is treated with the dual binding molecule by administering the dual binding molecule to the subject.

12. A method for treating cancer, comprising
administering a dual binding molecule to a subject in need of the prevention or treatment of a cancer,
wherein the dual binding molecule comprises a first binding domain which binds to a driver membrane protein and a second binding domain which binds to a target membrane protein,
the driver membrane protein and target membrane protein are located on the same cell membrane of a cell,
the driver membrane protein is c-Met,
the target membrane protein is HER-2 or EGFR,
the first binding domain comprises an anti-c-Met antibody or antigen-binding antibody fragment thereof that specifically binds to an epitope comprising 5 or more contiguous amino acids within the SEMA domain of c-Met protein comprising the amino acid sequence of SEQ ID NO: 73,
and the second binding domain comprises an anti-HER2 or anti-EGFR antibody, antigen-binding antibody fragment thereof, or DARPin against HER2 or EGFR;
and wherein the driver membrane protein and target membrane protein are internalized into the cell and degraded when the first binding domain of the dual binding molecule binds the driver membrane protein and the second binding domain binds the target membrane protein.

* * * * *